US007250074B2

United States Patent
Tonkovich et al.

(10) Patent No.: US 7,250,074 B2
(45) Date of Patent: *Jul. 31, 2007

(54) PROCESS FOR SEPARATING NITROGEN FROM METHANE USING MICROCHANNEL PROCESS TECHNOLOGY

(75) Inventors: Anna Lee Tonkovich, Marysville, OH (US); Dongming Qiu, Dublin, OH (US); Terence Andrew Dritz, Worthington, OH (US); Paul Neagle, Westerville, OH (US); Robert Dwayne Litt, Westerville, OH (US); Ravi Arora, Dublin, OH (US); Michael Jay Lamont, Hilliard, OH (US); Kristina M. Pagnotto, Cincinnati, OH (US)

(73) Assignee: Velocys, Inc., Plain City, OH (US)

( * ) Notice: Subject to any disclaimer, the term of this patent is extended or adjusted under 35 U.S.C. 154(b) by 338 days.

This patent is subject to a terminal disclaimer.

(21) Appl. No.: 10/927,370

(22) Filed: Aug. 26, 2004

(65) Prior Publication Data

US 2005/0045030 A1  Mar. 3, 2005

Related U.S. Application Data

(60) Provisional application No. 60/557,320, filed on Mar. 29, 2004, provisional application No. 60/498,892, filed on Aug. 29, 2003.

(51) Int. Cl.
*B01D 53/04* (2006.01)
(52) U.S. Cl. ............. 95/130; 95/143; 95/148; 95/903
(58) Field of Classification Search .......... 95/90, 95/96, 106, 114, 115, 130, 143, 148, 903; 96/126, 131
See application file for complete search history.

(56) References Cited

U.S. PATENT DOCUMENTS 3,710,547 A  1/1973  Nelson ............. 55/58

(Continued)

FOREIGN PATENT DOCUMENTS

DE  100 09 059 A1  2/2000

(Continued)

OTHER PUBLICATIONS

International Preliminary Examination Report; Application No. PCT/US2004/027787; mailed Aug. 5, 2005.

(Continued)

*Primary Examiner*—Frank M. Lawrence
(74) *Attorney, Agent, or Firm*—Renner, Otto, Boisselle & Sklar, LLP

(57) ABSTRACT

The disclosed invention relates to a process for separating methane or nitrogen from a fluid mixture comprising methane and nitrogen, the process comprising: (A) flowing the fluid mixture into a microchannel separator, the microchannel separator comprising a plurality of process microchannels containing a sorption medium, the fluid mixture being maintained in the microchannel separator until at least part of the methane or nitrogen is sorbed by the sorption medium, and removing non-sorbed parts of the fluid mixture from the microchannel separator; and (B) desorbing the methane or nitrogen from the sorption medium and removing the desorbed methane or nitrogen from the microchannel separator. The process is suitable for upgrading methane from coal mines, landfills, and other sub-quality sources.

57 Claims, 7 Drawing Sheets

U.S. PATENT DOCUMENTS

| | | | | |
|---|---|---|---|---|
| 4,723,966 | A | * | 2/1988 | Fuderer .......................... 95/98 |
| 4,909,924 | A | | 3/1990 | Raatz et al. ................. 208/111 |
| 4,960,450 | A | | 10/1990 | Schwarz et al. ............... 62/18 |
| 5,174,796 | A | | 12/1992 | Davis et al. .................... 55/26 |
| 5,268,023 | A | | 12/1993 | Kirner .......................... 95/103 |
| 5,385,876 | A | | 1/1995 | Schwarz et al. ............... 502/80 |
| 5,614,460 | A | | 3/1997 | Schwarz et al. ............. 502/418 |
| 5,726,118 | A | | 3/1998 | Ivey et al. ................... 502/417 |
| 5,792,239 | A | | 8/1998 | Reinhold, III et al. ......... 95/101 |
| 5,837,741 | A | | 11/1998 | Schwarz et al. ............. 521/124 |
| 5,989,316 | A | | 11/1999 | Kuznicki et al. ............. 95/130 |
| 6,090,738 | A | * | 7/2000 | Choudary et al. ............ 502/62 |
| 6,093,379 | A | | 7/2000 | Golden et al. .............. 423/230 |
| 6,197,092 | B1 | | 3/2001 | Butwell et al. ................. 95/96 |
| 6,205,793 | B1 | | 3/2001 | Schimp ....................... 62/46.1 |
| 6,225,257 | B1 | | 5/2001 | Putyera et al. ............. 502/432 |
| 6,336,956 | B1 | | 1/2002 | Moreau et al. ................. 95/96 |
| 6,444,012 | B1 | | 9/2002 | Dolan et al. .................... 95/99 |
| 6,497,750 | B2 | | 12/2002 | Butwell et al. ................. 95/96 |
| 6,508,862 | B1 | | 1/2003 | Tonkovich et al. ........... 95/106 |
| 6,652,627 | B1 | * | 11/2003 | Tonkovich et al. ........... 95/104 |
| 6,675,875 | B1 | | 1/2004 | Vafai et al. ................. 165/80.4 |
| 6,746,515 | B2 | * | 6/2004 | Wegeng et al. ................. 95/96 |
| 6,746,819 | B1 | | 6/2004 | Schmitz et al. .......... 430/272.1 |
| 6,747,178 | B1 | | 6/2004 | Harston et al. ............. 570/175 |
| 6,749,814 | B1 | | 6/2004 | Bergh et al. ................. 422/130 |
| 6,749,817 | B1 | | 6/2004 | Mulvaney, III ............. 422/200 |
| 6,755,211 | B1 | | 6/2004 | O'Connor et al. ........... 137/554 |
| 6,769,444 | B2 | | 8/2004 | Guzman et al. ......... 137/15.01 |
| 6,770,245 | B2 | | 8/2004 | Akporiaye et al. ...... 422/82.12 |
| 6,773,684 | B2 | | 8/2004 | Lesieur et al. .............. 422/198 |
| 6,990,290 | B2 | | 1/2006 | Kylberg et al. ............. 392/465 |
| 2004/0104010 | A1 | | 6/2004 | Kenny et al. .............. 165/80.4 |
| 2004/0107831 | A1 | | 6/2004 | Graham et al. ................. 95/96 |
| 2004/0123626 | A1 | | 7/2004 | Caze et al. ................... 65/17.2 |
| 2004/0125689 | A1 | | 7/2004 | Ehrfeld et al. ........... 366/165.1 |
| 2004/0130057 | A1 | | 7/2004 | Mehrabi et al. ....... 264/171.13 |
| 2004/0131345 | A1 | | 7/2004 | Kylberg et al. ............. 392/465 |
| 2004/0131507 | A1 | | 7/2004 | Saitmacher et al. ........ 422/111 |
| 2004/0131829 | A1 | | 7/2004 | Joseph et al. ............... 428/166 |
| 2004/0136902 | A1 | | 7/2004 | Plath et al. ................. 423/629 |
| 2004/0141893 | A1 | | 7/2004 | Martin ....................... 422/198 |
| 2004/0143059 | A1 | | 7/2004 | Cabrera ...................... 524/800 |
| 2004/0144421 | A1 | | 7/2004 | Parce et al. .................... 137/14 |
| 2004/0156762 | A1 | | 8/2004 | Schuppich et al. ......... 422/191 |
| 2005/0032240 | A1 | | 2/2005 | Lee et al. ................... 436/180 |

FOREIGN PATENT DOCUMENTS

| | | |
|---|---|---|
| DE | 100 09 059 A1 | 9/2000 |
| EP | 1 311 341 B1 | 8/2001 |
| WO | 03/026788 | 4/2003 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067708 | 8/2004 |
| WO | 2004/167160 | 8/2004 |

OTHER PUBLICATIONS

Sear Report and Written Opinion, Application No. PCT/US2004/027787, mailed Apr. 20, 2005.

Dong et al.; "A New Concept in the Design of Pressure-Swing Adsorption Processes for Multicomponent Gas Mixtures"; *Ind. Eng. Chem. Res.*; vol. 38; pp. 233-239; 1999.

Park et al.; "Adsorber Dynamics and Optimal Design of Layered Beds for Multicomponent Gas Adsorption"; *Chemical Engineering Science*, Vo. 53, No. 23, pp. 3951-3963; 1998.

Cracknell et al.; "Adsorption and Selectivity of Carbon Dioxide with Methane and Nitrogen in Slip-Shaped Carbonaceous Micropores: Stimulation and Experiment"; *Adsorption*; Vo. 2; pp. 193-203; 1996.

Heuchel et al.; "Adsorption of Carbon Dioxide and Methane and Their Mixtures on an Activated Carbon Simulation and Experiment"; *Langmuir*, vol. 15, No. 25, 1999.

Harlick et al.; "Adsorption of Carbon Dioxide, Methane, and Nitrogen: Pure and Binary Mixture Adsorption by ZSM-5 with $SiO_2/Al_2O_3$ Ratio of 30"; *Separation and Science and Technology*, vol. 37(1); pp. 33-60; 2002.

Yun et al.; "Adsorption of Methane, Ethane, and Their Binary Mixtures on MCM-41: Experimental Evaluation of Methods for the Prediction of Adsorption Equilibrium"; *Langmuir*; vol. 18; No. 7, 2002.

Sudibandriyo et al.; "Adsorption of Methane, Nitrogen, Carbon Dioxide, and Their Binary Mixtures on Dry Activated Carbon at 318.2 K and Pressures up to 13.6 MPa"; *Langmuir*; vol. 19; No. 13, pp. 5323-5331; 2003.

Sakoda et al.; "Adsorption of Methane onto Activated Carbon by a Graphite Crystal Aggregate Model"; *Fundamentals of Adsorption*; pp. 781-788; 1996.

Predescu et al.; "Adsorption of Nitrogen, Methane, Carbon Monoxide, and Their Binary Mixtures on Aluminophosphate Molecular Sieves"; *Adsorption*; vol. 3, pp. 7-25; 1996.

Braeuer et al.; "Calculation of Single Adsorption Isotherms from Gravimetrically Measured Binary Gas Mixture Adsorption Isotherms on Activated Carbon at High Pressures"; *Separation and Purification Technology*; Vo. 12; pp. 255-263; 1997.

Sweatman et al.; "Characterization of Porous Materials by Gas Adsorption at Ambient Temperatures and High Pressure"; *J. Phys. Chem. B.*; vol. 105, No. 7; pp. 1403-1411; 2001.

Gomes et al.; "Coalseam Methane Recovery by Vacuum Swing Adsorption"; *Separation and Purification Technology*; vol. 24; pp. 189-196; 2001.

Chihara et al.; "Control of Adsorption Rate on Zeolite by Chemical Vapor Deposition"; *Fundamentals of Adsorption*; 1996.

Sun et al.; "Correlating $N_2$ and $CH_4$ Adsorption on Microporous Carbon Using a New analytical Model"; *Energy & Fuels*; vol. 12, No. 6; 1998.

Jacquinot et al.; "Determination of Methane and other Small Hydrocarbons with a Platinum-Nafion Electrode by Stripping Voltammetry"; *Analytical Checmica Acta*; pp. 1-10; 2001.

Davies et al.; Development and Validation of Pore Structure Models for Adsorption in Activated Carbons; *Langmuir*, vol. 15, No. 19; 1999.

Buczek; "Development of Texture of Carbonaceous Sorbent for use in Methane Recovery from Gaseous Mixtures"; *Inzynieria Chemiczna I Procesowal*; vol. 21; pp. 385-392; 2000.

Warmuzinski et al.; "Effect of Adsorption Pressure on Methane Purity during PSA Separations of $CH_4/N_2$ Mixtures"; *Chemical Engineering and Processing*; vol. 38; pp. 55-60; 1999.

Kulkami et al.; "Enrichment of Methane Concentration via Separation of Gases using Vortex Tubes"; *Journal of Energy Engineering*; pp. 1-12; 2002.

Hoover et al.; "Gas Compression Using Temperature Swing Adsorption"; *Separation Science and Technology*; 37(14); pp. 3187-3199; 2002.

Roualdes et al.; "Gas Diffusion and Sorption Properties of Polysiloxane Membranes Prepared by PECVD"; *Journal of Membrane Science*; 198; pp. 299-310; 2002.

Mogri et al.; "Gas Sorption and Transport in Side-Chain Crystalline and Molten Poly(octadecyl acrylate)"; *Polymer*; vol. 42; pp. 2531-2542; 2001.

Wang et al.; "Gas Transport and Sorption in Polyaniline Thin Film"; *Synthetic Metals*; vol. 102; pp. 1333-1334; 1999.

Puziy et al.; "Heterogeneity of Synthetic Carbons Obtained from Polyimides"; *Applied Surface Science*; vol. 196; pp. 89-97; 2002.

Mentasty et al.; "High Pressure Methane Adsorption on NaX and NaY Zeolites with Different Si/Al Ratios"; *Adsorption Science Technology*; vo. 11; pp. 209-216; 1994.

Jayaraman et al.; "Kinetic Separation of Methane/Carbon Dioxide by Molecular Sieve Carbons"; *Separation Science and Technology*; vol. 37(11); pp. 2505-2528; 2002.

Olajossy et al.; "Methane Separation from Coal Mine Methane Gas by Vacuum Pressure Swing Adsorption"; *Chemical Engineering Research & Design*; vol. 81; pp. 474-482; 2003.

Ustinov et al.; "Modeling of Gas Adsorption Equilibrium Over a Wide Range of Pressure: A Thermodynamic Approach Based on Equation of State"; *Journal of Colloid and Interface Sciencel*; vol. 250; pp. 49-62; 2002.

Puziy et al.; "Modeling of High-Pressure Adsorption Using the Bender Equation of State"; *Langmuir*; vol. 19; pp. 314-320; 2003.

Park et al.; "Numerical Analysis on the Power Consumption of the PSA Process for Recovering $CO_2$ from Flue Gas"; *Ind. Eng. Chem. Res.*; vol. 41; pp. 4122-4131; 2002.

Sun et al.; "Predicing $CH_4$ Adsorption Capacity of Microporous Carbon Using $N_2$ Isotherm and a New Analytical Model"; *American Chemical Society, Division of Fuel Chemistry*; vol. 43; pp. 596-600; 1998.

Fuertes; "Preparation and Characterization of Adsorption-Selective Carbon Membranes for Gas Separation"; *Adsorption*; Vo. 7; pp. 117-129; 2001.

Takeuchi et al.; "Production of Tasty Drinking Water by Activated Carbon Adsorption Followed by Contact with Some Natural Ores"; $7^{th}$ Conference Asia Pac. Fonfed. Chem. Eng. $21^{st}$ Autralas, Chem. Eng. Conf.; pp. 527-532; 1993.

Rittig et al.; "Pure and Mixed-Gas Sorption Measurements on Zeolitic Adsorbents via Gas-Phase Nuclear Magnetic Resonance"; *Ind. Eng. Chem. Res.*; vol. 41; pp. 4430-4434; 2002.

Qinglin et al.; "Revisiting Transport of Gases in the Micropores of Carbon Molecular Sieves"; *Langmuir*, vol. 19; pp. 393-405; 2003.

Melnitchenko et al.; "Selective Gas Adsorption by Metal Exchanged Amorphous Kaolinite Derivatives"; *Applied Clay Science*; vol. 17; pp. 35-53; 2000.

Fatehi et al.; "Separation of Methane Nitrogen Mixtures by Pressure Swing Adsorption using a Carbon Molecular Sieve"; *Adsorption Science and Technology*; vol. 9; pp. 199-204; 1995.

Zhou et al.; "Studies on the Physical Adsorption Equilibria of Gases on Porous Solids over a Wide Temperature Range Spanning the Critical Region—Adsorption on Microporous Activated Carbon"; *Chinese Journal of Chemistry*; vol. 19; pp. 943-948; 2001.

Quinn; "Supercritical Adsorption of 'Permanent' Gases Under Corresponding States on Various Carbons"; *Carbon*; vol. 40; pp. 2767-2773; 2002.

Barton et al.; "Tailored Porous Materials"; *Chem. Mater.*; vol. 11; pp. 2633-2638; 1999.

"The Role of Quaternary Directing Agents"; *Chem. Mater.*; vol. 11, pp. 2639-2653; 1999.

Pires; "Textural and Surface Chemistry Characterization of Zeolites via Adsorption Phenomena"; *Handbook of Surfaces and Interfaces of Materials*; pp. 481-507; 2001.

Kluson et al.; "The Design of Microporous Graphitic Adsorbents for Selective Separation of Gases"; *Separation and Purification Technology*; vol. 20; pp. 15-24; 2000.

Clarkson et al.; "The Effect of Pore and Gas Pressure Upon the Transport Properties of Coal: a Laboratory and Modeling Study. I. Isotherms and Pore Volume Distributions"; *Fuel*; pp. 1333-1344; 1999.

Salem et al.; "Thermodynamics of High-Pressure Adsorption of Argon, Nitrogen, and Methane on Microporous Adsorbents"; *Langmuir*, vol. 14; pp. 3376-3389; 1998.

Maksymovych; "Investigation of the Influence of added Platinum on abilities of Methane Adsorption Semiconductor Sensors"; *Advances in Science and Technology*; vol. 26, pp. 311-316; 1999.

Choso et al.; "Dissociative Adsorption and Subsequent Reactions on Methane on Ar-ion Sputtered Single Crystal of $LiNbO3$"; *Journal of Molecular Catalysis A: Chemical*pp. 225-231; 1998, abstract.

Baronskaya et al.; "Ethylene Recovery from the Gas Product of Methane Oxidative Coupling by Temperature Swing Adsorption"; *Gas Separation & Purification*; vol. 10; pp. 85-88, 1996, abstract.

Triebe et al.; "Adsorption of Methane, Ethane and Ethylene on Molecular Sieve Zeolites"; *Gas Separation & Purification*; vol. 10; pp. 81-84; 1996, abstract.

Rychlicki et al.; "Methane Adsorption of Microporous activated Carbons"; *Polish Journal of Chemistry*; vol. 69; pp. 1328-1334; 1995, abstract.

Amankwah et al.; "Storage of Energy Gases on Activated Carbon on the Basis of Structural Parameters and Energetic Heterogeneity as Determined by High Pressure Adsorption of Methane and Hydrogen"; 1994; 163 pp. Avail.: Univ. Microfilms Int., Order No. DA9522510, From Diss. Abstr. Int., B 1995, 56(3), 1566, abstract.

Pan; "Pore Structure Alteration of a Carbon Moledular Sieve for the Separation of Hydrogen Sulfide from Methane by Adsorption"; *Adsorption Science and Technology*; vol. 10; pp. 193-201; 1993, abstract.

Choi et al.; "Adsorption Equilibria of Methane, Ethane, Ethylene, Nitrogen, and Hydrogen onto Activated Carbon"; *J. Chem. Eng. Data*; 2003; 48; pp. 603-607.

Chau et al.; "Zeolite Micromembranes"; *Lab Chip*; 2003; 3, pp. 53-55.

Qinglin et al.; "Binary and Ternary Adsorption Kinetics of Gases in Carbon Molecular Sieves"; *Langmuir*; 2003; 19; pp. 5722-5734.

Molina-Sabio et al.; "Phosphoric Acid Activated Carbon Discs for Methane Adsorption"; *Carbon*; 41; 2003; pp. 2113-2119.

Uraki et al.; "Activated Carbon Sheet Prepared from Softwood Acetic Acid Lignin"; *J. Wood Sci*; 2000; pp. 46:52-58.

Zhou et al.; "A Feasibility Study of Separating $CH_4$ /$N_2$ by Adsorption"; *Chinese J. Ch. E.* 10 (5) 558; 2002.

Besser, Ronald S. "New Directions in Reactor Design Through Miniaturization". Sep. 13, 2002, Tulane Engineering Forum.

Ouyang et al. "Flexible Microreactor System for Chemical Research at Moderate and High Temperatures". Stevens Institute of Technology.

Ouyang et al. "Flexible Microreactor System for Chemical Research at Moderate and High Temperatures". Stevens Institute of Technology, no date given.

\* cited by examiner

PROCESS FOR SEPARATING NITROGEN FROM METHANE USING MICROCHANNEL PROCESS TECHNOLOGY

This application claims priority to U.S. Provisional Applications 60/498,892, filed Aug. 29, 2003, and 60/557,320, filed Mar. 29, 2004. The disclosures in these applications are incorporated herein by reference.

This invention was made with Government support under Contract DE-FC26-03NT41905 awarded by the United States Department of Energy. The Government has certain rights in this invention.

TECHNICAL FIELD

This invention relates to a process for separating methane or nitrogen from a fluid mixture comprising methane and nitrogen using microchannel process technology. This invention is particularly suitable for upgrading sub-quality methane gas from coal mines, landfills, and other sub-quality sources.

BACKGROUND

Methane emissions from various sources represent a significant portion of non-$CO_2$ greenhouse gas emissions. Traditionally, coal mine and landfill operators have been able to recover only a small percentage of dilute methane gas streams because they contain significant quantities of contaminants, such as $CO_2$, oxygen, water vapor, and nitrogen. The cost of conventional gas separation systems, in particular nitrogen removal units, represents one of the most significant hurdles to mitigating non-$CO_2$ greenhouse emissions. Removal of methane from sub-quality sources has the potential to reduce annual greenhouse gas emissions by about 23.5 billion equivalent kilograms of $CO_2$ and to enable the cost-effective recovery of about 3.5 trillion cubic feet per year of natural gas. This represents a reduction of about 0.3% in annual U.S. greenhouse gas emissions at no net cost when the value of pipeline quality natural gas is realized.

Four commercial methods are currently used to remove nitrogen from natural gas: cryogenic distillation, pressure swing adsorption (PSA), lean oil absorption, and membrane separation. Cryogenic distillation involves the condensation of dry natural gas, followed by distillation of nitrogen at very low temperatures (e.g., about −150° C.). This technique is used commercially to separate nitrogen from natural gas. Although methane recovery is high, there is a significant pretreatment cost (water and $CO_2$ removal). In addition, the complexity of the system makes reliability an issue. Cryogenic distillation is generally more cost-effective at large capacities (e.g., about 75 million standard cubic feet per day (MMSCFD)), while most coal mine and landfill opportunities are typically in the 2-10 MMSCFD capacity range. Cryogenic distillation also requires significant energy to compress the gas stream.

In most conventional PSA processes, methane is selectively adsorbed onto carbon sieves, leaving nitrogen in the raffinate. Pretreatment and multiple beds are required, which leads to high capital costs. This method also requires methane to be recompressed and is inflexible to variations in flow rates. PSA has been used on a limited commercial basis for nitrogen separation and is best suited for low (e.g., about 2 to 10 MMSCFD) gas flow rates and high nitrogen content.

The lean oil absorption process involves the absorption of methane in chilled hydrocarbon oil. This process is energy-intensive and, therefore, has high processing costs. In addition, the large equipment used for this process makes redeployment unlikely.

Membrane separation involves separating nitrogen from natural gas by a process wherein the methane selectively permeates through a membrane, and the raffinate is a nitrogen-rich stream that can be burned to run a permeate compressor. Membranes have a low methane recovery (e.g., about 80%) that makes them less attractive.

SUMMARY

The present invention, in at least one embodiment, provides a solution to one or more of the problems presented by the prior art. The invention relates to a sorption/desorption process for separating nitrogen or methane from a fluid mixture comprising nitrogen and methane. This process may be used in upgrading sub-quality methane sources such as coal mine methane gases (e.g., gob gas), landfill methane gases, and the like. Unlike other processes directed to the separation of nitrogen from methane, in one embodiment of this invention, capital-intensive operations for product recompression are not required. This provides the inventive process with significant cost advantages. The inventive process may have lower capital operating costs as compared to membrane separation systems. This lower cost may allow for marginal natural gas sources to be economically upgraded and utilized. The inventive process also offers a modular approach that allows units to be redeployed, which is difficult for equipment intensive processes such as cryogenic distillation and lean oil absorption. The inventive process may be operated over a wide range of flow rates which makes it applicable to numerous applications.

This invention relates to a process for separating methane or nitrogen from a fluid mixture comprising methane and nitrogen, the process comprising:

(A) flowing the fluid mixture into a microchannel separator, the microchannel separator comprising a plurality of process microchannels containing a sorption medium, the fluid mixture being maintained in the microchannel separator until at least part of the methane or nitrogen is sorbed by the sorption medium, and removing non-sorbed parts of the fluid mixture from the microchannel separator; and (B) desorbing methane or nitrogen from the sorption medium and removing the desorbed methane or nitrogen from the microchannel separator.

In one embodiment, the non-sorbed parts of the fluid mixture may be removed during step (A) by flowing a purging fluid through the process microchannels. In one embodiment, the desorbed methane or nitrogen may be removed during step (B) by flowing a flush fluid through the process microchannels. In one embodiment, a pressure differential and/or temperature gradient may be applied across the process microchannels to drive the non-sorbed parts of the fluid mixture during step (A) and/or the desorbed methane or nitrogen during step (B) out of the process microchannels. In one embodiment, a tail gas comprising methane and optionally nitrogen may be produced during step (A). This tail gas may be used as a source of energy.

In one embodiment, methane is sorbed by the sorption medium during step (A). In one embodiment, nitrogen is sorbed by the sorption medium during step (A).

In one embodiment, the process microchannels exchange heat with a heat exchanger. The heat exchanger may comprise heat exchange channels for heating and/or cooling the process microchannels. The heat exchanger may comprise a resistance heater for heating the process microchannels. The heat exchange channels and/or resistance heater may be positioned remotely from the process microchannels or they may be positioned adjacent to the process microchannels. The heat exchange channels may be microchannels. The flow of heat exchange fluid through the heat exchange channels may be cocurrent, counter-current or cross-current relative to the flow of fluid through the process microchannels.

In one embodiment, the temperature swings back and forth from one temperature during step (A) of the inventive process to another temperature during step (B). As a result, this embodiment of the inventive process may be referred to as a temperature swing adsorption (TSA) process.

In one embodiment, during step (A) a purging fluid flows through the process microchannels to remove non-sorbed parts of the fluid mixture from the microchannel separator.

In one embodiment, during step (A) the temperature and/or pressure within the process microchannels is increased to remove non-sorbed parts of the fluid mixture from the microchannel separator.

In one embodiment, during step (B) a flush fluid flows through the process microchannels to remove desorbed methane or nitrogen from the microchannel separator.

In one embodiment, during step (B) the temperature and/or pressure within the process microchannels is increased to remove desorbed methane or nitrogen from the microchannel separator.

In one embodiment, the invention relates to a process for separating methane or nitrogen from a fluid mixture comprising methane and nitrogen, the process comprising:
  (I)(A) flowing part of the fluid mixture into a first microchannel separator, the first microchannel separator comprising a plurality of first process microchannels containing a first sorption medium, the fluid mixture being maintained in the first microchannel separator until at least part of the methane or nitrogen is sorbed by the first sorption medium, removing non-sorbed parts of the fluid mixture from the first microchannel separator;
  (I)(B) desorbing the methane or nitrogen from the first sorption medium and removing the desorbed methane or nitrogen from the first microchannel separator;
  (II)(A) flowing another part of the fluid mixture into a second microchannel separator, the second microchannel separator comprising a plurality of second process microchannels containing a second sorption medium, the fluid mixture being maintained in the second microchannel separator until at least part of the methane or nitrogen is sorbed by the second sorption medium, removing non-sorbed parts of the fluid mixture from the second microchannel separator; and
  (II)(B) desorbing methane or nitrogen from the second sorption medium and removing the desorbed methane or nitrogen from the second microchannel separator.

In one embodiment, step (I)(A) is conducted simultaneously with step (II)(B). In one embodiment, step (I)(B) is conducted simultaneously with step (II)(A). In one embodiment, methane is sorbed by the sorption medium during steps (I)(A) and (II)(A). In one embodiment, nitrogen is sorbed by the sorption medium during steps (I)(A) and (II)(A).

In one embodiment, the first microchannel separator and the second microchannel separator may be operated in a sequential manner and in combination with one or more heat exchangers to provide for heating in one of the microchannel separators and at the same time cooling in the other microchannel separator, followed in sequence by a reversal from heating to cooling or cooling to heating in the microchannel separators. For example, the inventive process may be operated as a TSA process with cooling during step (I)(A) of the inventive process in the first microchannel separator in combination with heating during step (II)(B) of the inventive process in the second microchannel separator, followed by a reversal from cooling to heating in the first microchannel separator to effect step (I)(B) of the inventive process and from heating to cooling in the second microchannel separator to effect step (II)(A) of the inventive process. In this embodiment, steps (I)(A) and (II)(B) may be conducted simultaneously, and steps (I)(B) and (II)(A) may be conducted simultaneously. In one embodiment, this process provides the advantage of significant savings in energy usage.

In one embodiment, the invention relates to a process for separating methane or nitrogen from a fluid mixture comprising methane and nitrogen, the process comprising:
  (I)(A) flowing the fluid mixture into a first microchannel separator, the first microchannel separator comprising a plurality of first process microchannels containing a first sorption medium, the fluid mixture being maintained in the first microchannel separator until at least part of the methane or nitrogen is sorbed by the first sorption medium, removing non-sorbed parts of the fluid mixture from the first microchannel separator, the non-sorbed parts of the fluid mixture removed from the first microchannel separator containing methane or nitrogen;
  (I)(B) desorbing methane or nitrogen from the first sorption medium and removing the desorbed methane or nitrogen from the first microchannel separator;
  (II)(A) flowing non-sorbed parts of the fluid mixture removed from the first microchannel separator during step (I)(A) into a second microchannel separator, the second microchannel separator comprising a plurality of second process microchannels containing a second sorption medium, the non-sorbed parts of the fluid mixture being maintained in the second microchannel separator until at least part of the methane or nitrogen is sorbed by the second sorption medium, removing non-sorbed parts of the fluid mixture from the second microchannel separator; and
  (II)(B) desorbing methane or nitrogen from the second sorption medium and removing the desorbed methane or nitrogen from the second microchannel separator.

In one embodiment, methane is sorbed by the sorption medium during steps (I)(A) and (II)(A). In one embodiment, nitrogen is sorbed by the sorption medium during steps (I)(A) and (II)(A).

In one embodiment, the invention relates to a process for upgrading sub-quality methane gas wherein the sub-quality methane gas comprises methane and nitrogen, the process comprising: (A) flowing the sub-quality methane gas into a microchannel separator, the microchannel separator comprising a plurality of process microchannels containing a sorption medium, the sub-quality methane gas being maintained in the microchannel separator until at least part of the methane is sorbed by the sorption medium, and removing non-sorbed parts of the sub-quality methane gas from the microchannel separator; and (B) desorbing the methane from the sorption medium and removing the desorbed methane from the microchannel separator.

BRIEF DESCRIPTION OF THE DRAWINGS

In the annexed drawings, like parts and features have like designations.

DETAILED DESCRIPTION

Figure 1:
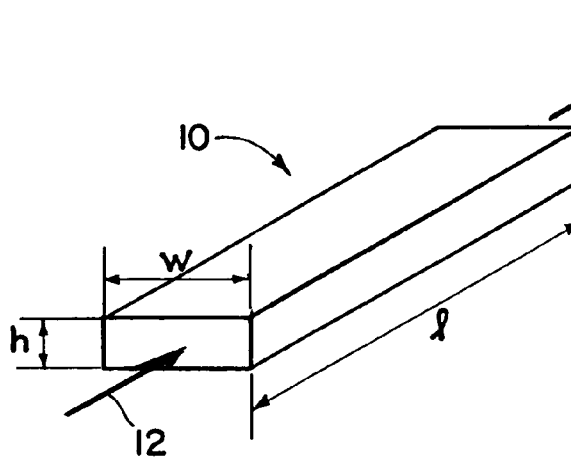
FIG. 1 is a schematic illustration of a microchannel useful with the inventive process.

The term "microchannel" refers to a channel having at least one internal dimension of height or width of up to about 10 millimeters (mm), and in one embodiment up to about 5 mm, and in one embodiment up to about 2 mm, and in one embodiment up to about 1 mm. An example of a microchannel that may be used with the inventive process as a process microchannel and/or a heat exchange microchannel is illustrated in FIG. 1. Referring to FIG. 1, microchannel 10 has a height (h), width (w) and length (l). Fluid flows through the microchannel 10 in the direction indicated by arrows 12 and 14. Both the height (h) and width (w) are perpendicular to the flow of fluid through the microchannel 10. The height (h) or width (w) of the microchannel may be in the range of about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.75 mm, and in one embodiment about 0.05 to about 0.5 mm. The other dimension of height (h) or width (w) may be of any dimension, for example, up to about 3 meters, and in one embodiment about 0.01 to about 3 meters, and in one embodiment about 0.1 to about 3 meters. The length (l) of the microchannel may be of any dimension, for example, up to about 10 meters, and in one embodiment about 0.2 to about 10 meters, and in one embodiment from about 0.2 to about 6 meters, and in one embodiment from 0.2 to about 3 meters. Although the microchannel illustrated in FIG. 1 has a cross section that is rectangular, it is to be understood that the microchannel may have a cross section having any shape, for example, a square, circle, semi-circle, trapezoid, etc. The shape and/or size of the cross section of the microchannel may vary over its length. For example, the height or width may taper from a relatively large dimension to a relatively small dimension, or vice versa, over the length of the microchannel.

The term "adjacent" when referring to the position of one channel relative to the position of another channel means directly adjacent such that a wall separates the two channels. This wall may vary in thickness. However, "adjacent" channels are not separated by an intervening channel that would interfere with heat transfer between the channels.

The term "fluid" refers to a gas, a liquid, or a gas or a liquid containing dispersed solids, or a mixture thereof. The fluid may be in the form of a gas containing dispersed liquid droplets.

The term "residence time," which may also be referred to as the "average residence time," is the internal volume of a space occupied by a fluid flowing through the space divided by the average volumetric flowrate for the fluid flowing through the space at the temperature and pressure being used.

The term "cycle time" refers to the time period required to complete both steps (A) and (B) of the inventive process.

The term "sorb" refers to adsorption and/or absorption. In one embodiment, one molecule or sorbate has a preferential affinity to a solid sorbent over a second molecule or sorbate.

The term "average sorbent temperature" refers to the mean sorbent temperature at the end of either step (A) or step (B) of the inventive process, and prior to the commencement of the alternate step, that is, prior to the commencement of the alternating sequential step (B) or step (A). In one embodiment, the sorbent temperature may be measured at or near the entrance to the sorbent bed and at or near the exit from the sorbent bed. The average sorbent temperature may be the arithmetic mean of the temperatures measured at or near the entrance to the sorbent bed and at or near the exit from the sorbent bed.

The terms "standard cubic feet" or "standard cubic meters" refers to volumes measured at a temperature of 20° C. and atmospheric pressure.

The term "gauge pressure" refers to absolute pressure, less atmospheric pressure. For example, a gauge pressure of zero atmospheres corresponds to atmospheric pressure. However, throughout the text and in the appended claims, unless otherwise indicated, all pressures are absolute pressures.

The fluid mixture that may be treated pursuant to the inventive process may be any fluid mixture comprising methane and nitrogen. The fluid mixture may be a sub-quality methane gas such as coal mine methane gas, methane gas from landfills, and the like. The concentration of methane in the fluid mixture may be in the range from about 1 to about 98% by volume, and in one embodiment about 1 to about 75% by volume. The concentration of nitrogen may be in the range from about 1 to about 98% by volume, and in one embodiment about 4 to about 40% by volume. The fluid mixture may further comprise carbon dioxide. The concentration of carbon dioxide in the fluid mixture may be in the range from about 1 to about 50% by volume, and in one embodiment about 1 to about 30% by volume. The fluid mixture may contain additional components such as oxygen and water vapor. The concentration for each of these additional components may be in the range from about 0.01 to about 10% by volume, and in one embodiment about 0.1 to about 1% by volume. The fluid mixture may be derived from low BTU (British Thermal Unit) methane streams, such as those found in coal mines, landfills and other sub-quality sources. The fluid mixtures obtained from coal mines are sometimes referred to as coal mine gob gasses.

In one embodiment, the invention relates to a process for upgrading a sub-quality methane gas wherein the inventive sorption/desorption process is used to separate out the nitrogen. In one embodiment, the nitrogen may be separated using a microchannel TSA nitrogen rejection process. In one embodiment, oxygen, water vapor and carbon dioxide may be separated using conventional techniques. The oxygen may be separated using catalytic deoxygenation or oxygen adsorption techniques. The water may be separated using molecular sieves or dehydration. The carbon dioxide may be separated using amine separation, carbon dioxide adsorption or membrane separation. The sequence of these separations may follow any order. In one embodiment, water vapor may be separated out first, followed by nitrogen removal using the inventive sorption/desorption process, and then the oxygen and carbon dioxide may be removed.

Figure 2:
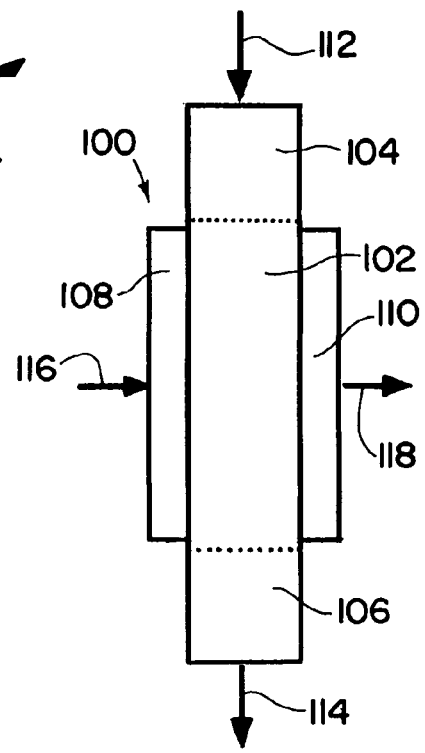
FIG. 2 is a schematic illustration of a microchannel separator which can be used pursuant to the inventive process to separate methane or nitrogen from a fluid mixture comprising methane and nitrogen.

The inventive sorption/desorption process will be described initially with reference to FIG. 2. Referring to FIG. 2, the process may be conducted using microchannel separator 100 which includes microchannel separator core 102, process header 104, process footer 106, heat exchange header 108 and heat exchange footer 110. The microchannel separator core 102 contains a plurality of process microchannels and a plurality of adjacent heat exchange channels. The heat exchange channels may be microchannels. A sorption medium is contained within the process microchannels. The process microchannels and heat exchange channels may be aligned in layers, one above the other, or side by side. In one embodiment, each layer of process microchannels is positioned between two layers of heat exchange channels, one of the layers of heat exchange channels being used for heating and the other layer of heat exchange channels being used for cooling. The process header 104 provides a passageway for fluid to flow into the process microchannels with an even or substantially even distribution of flow to the process microchannels. The process footer 106 provides a passageway for fluid to flow from the process microchannels 104 in a rapid manner with a relatively high rate of flow. A fluid mixture containing methane and nitrogen flows into microchannel separator 100, as indicated by directional arrow 112, through process header 104 and then into the process microchannels in the microchannel separator core 102 where it contacts the sorption medium. The fluid mixture is maintained in the process microchannels in contact with the sorption medium until at least part of either the methane or the nitrogen is sorbed by the sorption medium. The sorption of either methane or nitrogen with this process is dependent on whether the sorption medium has a preferential affinity for methane or nitrogen. The inventive process may be operated with either type of sorption medium. The non-sorbed parts of the fluid mixture are then removed from the process microchannels. In one embodiment, the non-sorbed parts of the fluid mixture may be removed from the process microchannels by flowing a purging fluid to and through the process header 104, as indicated by directional arrow 112, and then to and through the process microchannels to displace non-sorbed parts of the fluid mixture from the process microchannels. The non-sorbed parts of the fluid mixture and the purging fluid flow through the process microchannels to and through the process footer 106 and out of the microchannel separator 100 as indicated by directional arrow 114. In one embodiment, the non-sorbed parts of the fluid mixture may be removed from the process microchannels by applying a pressure differential and/or temperature gradient across the process microchannels sufficient to drive the non-sorbed parts of the fluid mixture out of the process microchannels. In one embodiment, a purging fluid in combination with a pressure differential and/or temperature gradient may be used to remove the non-sorbed parts of the fluid mixture from the process microchannels. The non-sorbed parts of the fluid mixture comprise methane or nitrogen, depending on which remains behind sorbed by the sorption medium. In one embodiment, the non-sorbed parts of the fluid mixture comprises nitrogen and a reduced level of methane; this non-sorbed gaseous mixture may be referred to as tail gas. The temperature within the process microchannels is then changed to provide for desorption of the methane or nitrogen from the sorption medium. The methane or nitrogen is desorbed from the sorption medium. The desorbed methane or nitrogen is then removed from the process microchannels. In one embodiment, the desorbed methane or nitrogen may be removed by flowing a flush fluid into the microchannel separator 100, as indicated by directional arrow 112, to and through process header 104 to the microchannels, and then through the microchannels to the process footer 106, and then out of the microchannel separator 100 as indicated by directional arrow 114. In one embodiment, the desorbed methane or nitrogen may be removed from the process microchannels by applying a pressure differential and/or temperature gradient across the process microchannels sufficient to drive the desorbed methane or nitrogen out of the process microchannels. In one embodiment, a purging fluid in combination with a pressure differential and/or temperature gradient may be used to remove the desorbed methane or nitrogen from the process microchannels. The non-sorbed fluid components may be recycled through the process microchannels or to other process microchannels connected in series any number of times, for example, one, two, three, four times, etc. A heat exchange fluid flows into heat exchange header 108, as indicated by directional arrow 116, and from heat exchange header 108 through the heat exchange channels in microchannel separator core 102 to heat exchange footer 110, and out of heat exchange footer 110, as indicated by directional arrow 118. The heat exchange fluid may be used to heat and cool the process microchannels. Alternatively, a resistance heater positioned within or adjacent to the process microchannels may be used to heat the process microchannels. The resistance heater may be in contact with the sorption medium. In one embodiment, the heat exchange fluid may be used to cool the process microchannels, and the resistance heater may be used to heat the process microchannels.

Figure 3:
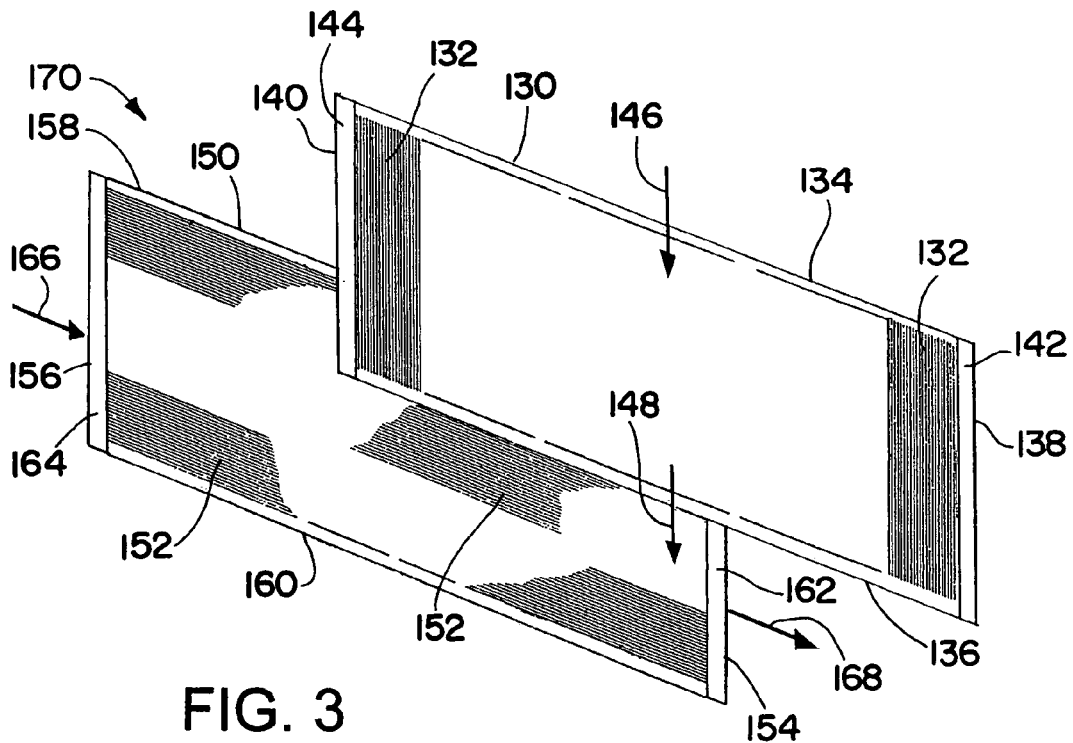
FIG. 3 is a schematic illustration of a layer of process microchannels and a layer of heat exchange microchannels that may be used in the microchannel separator core of the microchannel separator illustrated in FIG. 2.

In one embodiment, the microchannel separator core 102 may contain layers of process microchannels and heat exchange microchannels aligned side by side as illustrated in FIG. 3. Referring to FIG. 3, process microchannel layers 130 and heat exchange microchannel layers 150 are aligned side by side to provide repeating unit 170. Microchannel layer 130 provides for the flow of process fluid. Microchannel layer 150 provides for the flow of heat exchange fluid. In one embodiment, each microchannel layer 130 may be positioned between adjacent microchannel layers 150 positioned on each side of the microchannel layer 130, one of the microchannel layers 150 being used for heating and the other microchannel layer 150 being used for cooling.

Microchannel layer 130 contains a plurality of microchannels 132 aligned in parallel, each process microchannel 132 extending along the length of microchannel layer 130 from end 134 to end 136, the process microchannels 132 extending along the width of microchannel layer 130 from end 138 to end 140 of the microchannel layer 130. Bonding strips 142 and 144 are positioned at the ends 138 and 140, respectively, of microchannel layer 130 to permit bonding of the microchannel layer 130 to the next adjacent heat exchange layers 150. The sorption medium is contained within the process microchannels 132. The flow of process fluid through the process microchannels 132 may be in the direction indicated by arrows 146 and 148. Each of the process microchannels 132 may have a cross section having any shape, for example, a square, rectangle, circle, semi-circle, etc. Each process microchannel 132 may have an internal height or gap of up to about 10 mm, and in one embodiment up to about 6 mm, and in one embodiment up to about 4 mm, and in one embodiment up to about 2 mm. In one embodiment, the height or gap may be in the range of about 0.05 to about 10 mm, and in one embodiment about 0.05 to about 6 mm, and in one embodiment about 0.05 to about 4 mm, and in one embodiment about 0.05 to about 2 mm. The width of each of these microchannels may be of any dimension, for example, up to about 3 meters, and in one embodiment about 0.01 to about 3 meters, and in one embodiment about 0.1 to about 3 meters. The length of each process microchannel 132 may be of any dimension, for example, up to about 10 meters, and in one embodiment about 0.2 to about 10 meters, and in one embodiment about 0.2 to about 6 meters, and in one embodiment from 0.2 to about 3 meters.

Microchannel layer 150 contains a plurality of heat exchange microchannels 152 aligned in parallel, each heat exchange microchannel 152 extending along the width of microchannel layer 150 from end 154 to end 156, the heat exchange microchannels 152 extending along the length of microchannel layer 150 from end 158 to end 160 of microchannel layer 150. Bonding strips 162 and 164 are positioned at ends 154 and 156, respectively, of microchannel layer 150 to permit bonding of the microchannel layer 150 to the next adjacent process microchannel layers 130. The heat exchange fluid may flow through the heat exchange microchannels 152 in the direction indicated by arrows 166 and 168. The flow of heat exchange fluid in the direction indicated by arrows 166 and 168 is cross-current to the flow of process fluid flowing through process microchannels 132, as indicated by arrows 146 and 148. Alternatively, the heat exchange microchannels 152 could be oriented to provide for flow of the heat exchange fluid along the length of the microchannel layer 150 from end 158 to end 160 or from end 160 to end 158. This would result in the flow of heat exchange fluid in a direction that would be cocurrent or counter-current to the flow of process fluid through the process microchannels 132. Each of the heat exchange microchannels 152 may have a cross section having any shape, for example, a square, rectangle, circle, semi-circle, etc. Each of the heat exchange microchannels 152 may have an internal height or gap of up to about 2 mm, and in one embodiment in the range of about 0.05 to about 2 mm, and in one embodiment about 0.05 to about 1.5 mm. The width of each of these microchannels may be of any dimension, for example, up to about 3 meters, and in one embodiment from about 0.01 to about 3 meters, and in one embodiment about 0.1 to about 3 meters. The length of each of the heat exchange microchannels 152 may be of any dimension, for example, up to about 10 meters, and in one embodiment from about 0.2 to about 10 meters, and in one embodiment from about 0.2 to about 6 meters, and in one embodiment from 0.2 to about 3 meters.

Figure 4:
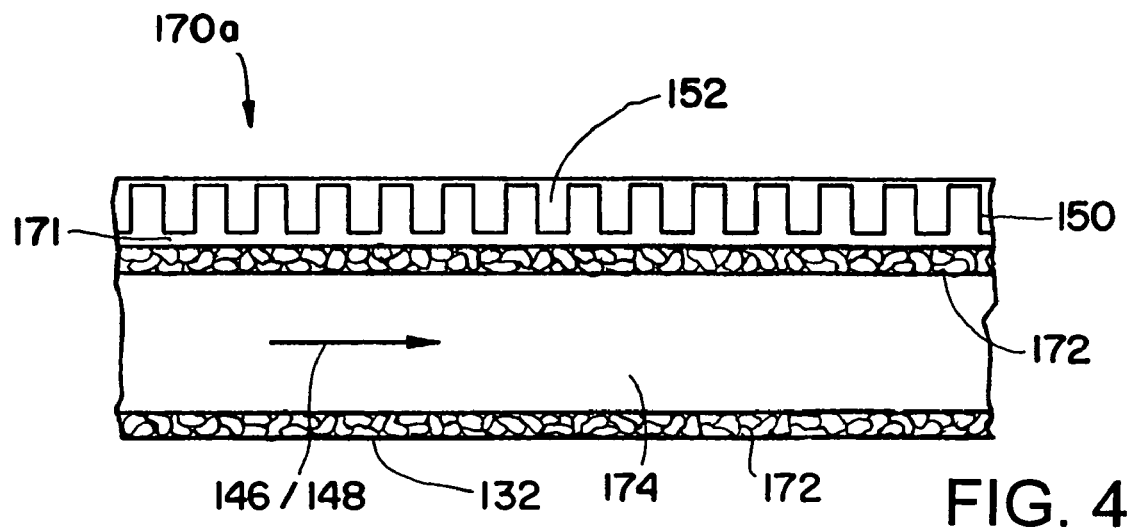
FIG. 4 is a schematic illustration of a process microchannel and adjacent heat exchange channels that may be used in the microchannel separator core of the microchannel separator illustrated in FIG. 2, the flow of heat exchange fluid through the heat exchange channels being cross-current relative to the flow of fluid through the process microchannel.

Repeating unit 170a is illustrated in FIG. 4. Referring to FIG. 4, process microchannel 132 is positioned adjacent to microchannel layer 150 which contains heat exchange microchannels 152. A common wall 171 separates the process microchannel 132 from the heat exchange microchannel layer 150. A sorption medium 172 is adhered to the upper and lower walls of process microchannel 132. A flow path 174 is provided between the layers of sorption medium 172. Process fluid flows through flow path 174 in process microchannel 132 in the direction indicated by directional arrow 146/148 and contacts sorption medium 172. Heat exchange fluid flows through the heat exchange microchannels 152 in a direction that is cross-current to the flow of process fluid through the microchannel 132.

Figure 5:
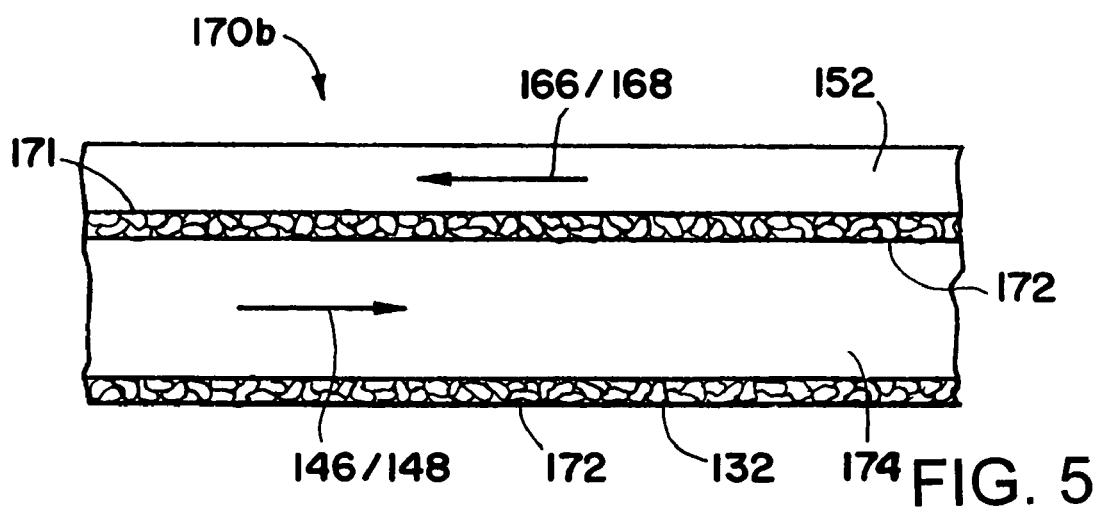
FIG. 5 is a schematic illustration of a process microchannel and an adjacent heat exchange channel that may be used in the microchannel separator core of the microchannel separator illustrated in FIG. 2, the flow of heat exchange fluid through the heat exchange channel being counter-current relative to the flow of fluid through the process microchannel.

Repeating unit 170b illustrated in FIG. 5 is identical to the repeating unit 170a illustrated in FIG. 4 with the exception that the microchannel layer 150 is rotated 90° and the heat exchange fluid flowing through the heat exchange microchannel 152 flows in the direction indicated by direction arrow 166/168 which is countercurrent to the flow of process fluid through the microchannel 132, as indicated by directional arrow 146/148. Alternatively, the heat exchange fluid could flow in the direction opposite to that indicated by directional arrow 166/168 and thereby provide for the flow of heat exchange fluid through the heat exchange microchannel 152 in a direction that would be cocurrent relative to the direction of process fluid through the process microchannel 132.

Figure 16:
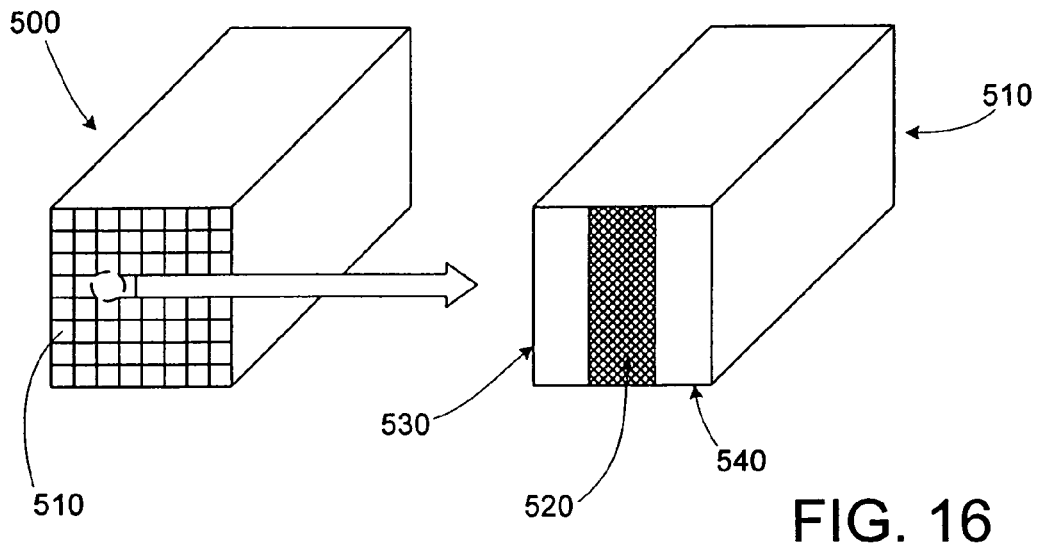
FIG. 16 is a schematic illustration of a microchannel TSA nitrogen rejection unit that can be used pursuant to the inventive process, and a drawing detail showing a schematic illustration of a repeating unit for the microchannel TSA nitrogen rejection unit.

The repeating units illustrated in FIG. 4 and FIG. 5 exemplify configurations wherein heating and cooling fluids flow alternatively through the same heat exchange channels. Alternatively, heating and cooling fluids may flow through separate heat exchange channels in repeating units which contain separate heat exchange channel(s) on each side of the process microchannel, the heat exchange channel(s) on one side of the process microchannel being used for cooling and the heat exchange channel(s) on the other side of the process microchannel being used for heating. This is illustrated in FIG. 16, which is discussed below.

The number of microchannels in each of the microchannel layers 130 and 150 may be any desired number, for example, one, two, three, four, five, six, eight, ten, hundreds, thousands, tens of thousands, hundreds of thousands, millions, etc. Similarly, the number of repeating units 170 (or 170a or 170b) of microchannel layers in the microchannel reactor core 102 may be any desired number, for example, one, two, three, four, six, eight, ten, hundreds, thousands, etc.

The microchannels 132 and 152 may have rectangular cross sections and be aligned in side-by-side vertically oriented interleaved planes or horizontally oriented interleaved stacked planes. These planes can be tilted at an inclined angle from the horizontal. These configurations may be referred to as parallel plate configurations. An array of these rectangular channels can be easily arranged in a modularized compact unit for scale-up.

The microchannel separator core 102, including the process microchannels 132 and heat exchange channels 152, process header 104, process footer 106, heat exchange header 108 and heat exchange footer 110 may be made of any material that provides sufficient strength, dimensional stability and heat transfer characteristics to permit operation of the inventive process. These materials include steel; aluminum, titanium; nickel, platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

The microchannel separator core 102 may be fabricated using known techniques including wire electrodischarge machining, conventional machining, laser cutting, photochemical machining, electrochemical machining, molding, water jet, stamping, etching (for example, chemical, photochemical or plasma etching) and combinations thereof.

The microchannel separator core 102 may be constructed by forming layers or sheets with portions removed that allow flow passage. A stack of sheets may be assembled via diffusion bonding, laser welding, diffusion brazing, and similar methods to form an integrated device. The microchannel separator core may be assembled using a combination of sheets or laminae and partial sheets or strips. In this method, the channels or void areas may be formed by assembling strips or partial sheets to reduce the amount of material required.

In one embodiment, subsections or modular units of the microchannel separator core 102 may be fabricated using the following components: a substrate piece with a hermetically sealed perimeter and open top/bottom for process flow; and a heat exchange piece. The substrate piece and heat exchange piece may be joined (welded, glued, soldered, etc.) to form a leak-free operating unit. The heat exchange piece may be extruded. The substrate piece and the heat exchange piece may be made from plastic, metal, or other materials as discussed above.

The microchannel separator 100 has appropriate manifolds, valves, conduit lines, etc. to control flow of the process fluid, and the flow of the heat exchange fluid. These are not shown in the drawings, but can be readily provided by those skilled in the art.

Referring to FIGS. 2-5, step (A) of the inventive process may be conducted by flowing the fluid mixture into microchannel separator 100, as indicated by direction arrow 112. In microchannel separator 100 the fluid mixture flows into and through header 104 to process microchannels 132, through the microchannels 132 in contact with sorption medium 172, and then to and through footer 106. The flow of the fluid mixture may be momentarily stopped within the process microchannels 132 to permit sorption of at least part of the methane or nitrogen by the sorption medium 172. The choice of sorption of either methane or nitrogen during this step is dependent upon the sorption medium employed. Process step (A) may be continued until a desired loading of the sorption medium 172 by the methane or nitrogen is achieved. The desired loading level may be in the range of about 0.001 to about 1 gram of methane or nitrogen per gram of sorption medium, and in one embodiment about 0.01 to about 0.1 gram of methane or nitrogen per gram of sorption medium. At the end of this sorption step the non-sorbed parts of the fluid mixture may be removed from the process microchannels. This may be done by flowing a purging fluid into the microchannel separator 100, as indicated by directional arrow 112. The purging fluid flows through process header 104, into process microchannels 132, through the microchannels 132 and then to and through footer 106 to displace the non-sorbed part of the fluid mixture from the microchannel separator 100. As an alternative to the foregoing, the purging fluid and the non-sorbed part of the fluid mixture may flow in the opposite direction through the process microchannels 132, that is, from footer 106 through the process microchannels 132 to the header 104. During the sorption part of step (A) of the inventive process, the average sorbent temperature within the process microchannels may be in the range from about −40° C. to about 200° C., and in one embodiment from about −40° C. to about 150° C., and in one embodiment from about 0° C. to about 200° C., and in one embodiment about 20° C. to about 60° C., and in one embodiment from about 30° C. to about 50° C., and in one embodiment about 40° C. The pressure within the process microchannels 132 during step (A) may be in the range from about 0.0001 to about 100 atmospheres of absolute pressure, and in one embodiment from about 0.01 to about 50 atmospheres, and in one embodiment from about 0.1 to about 30 atmospheres, and in one embodiment from about 1 to about 20 atmospheres, and in one embodiment from about 1 to about 10 atmospheres absolute pressure. The period of time for the sorption to occur may range from about 0.1 to about 10 seconds, and in one embodiment about 1 to about 5 seconds.

The process microchannels 132 may be purged by flowing a purging fluid through the process microchannels to remove the non-sorbed parts of the fluid mixture. During the purging step the average sorbent temperature within the process microchannels may be in the range from about −40° C. to about 200° C., and in one embodiment from about −40° C. to about 150° C., and in one embodiment from about 0° C. to about 200° C., and in one embodiment about 20° C. to about 60° C., and in one embodiment from about 30° C. to about 50° C., and in one embodiment about 40° C. The residence time for the purging fluid in the process microchannels 132 may range from about 0.1 to about 10 seconds, and in one embodiment about 1 to about 5 seconds.

Examples of purging fluids that may be used include methane, nitrogen, water, or a condensable fluid.

In one embodiment, the requirement for using purging fluid to remove the non-sorbed parts of the fluid mixture may be avoided. In this embodiment, the inlet valves may be closed, and the system heated. The resulting pressurization of the system pushes the non-sorbed parts of the fluid mixture out of the process microchannels. In one embodiment, a closed system may be employed where both the inlet and outlet valves are closed during heating, followed by opening the outlet valve to reduce the system pressure and remove the non-sorbed parts of the fluid mixture. The outlet valve may also stay open (inlet feed valve closed) during the heating step to begin to remove desorbed methane or nitrogen during all or part of the heating step. The heating time and temperature may be tuned to optimize performance. Higher purities and lower capital costs may be achieved with this embodiment. This approach may be used for evaluating adsorbent performance under fast thermal cycle conditions.

In one embodiment, parts of the fluid mixture in the process microchannels may be removed using a pressure differential and/or temperature gradient applied across the process microchannels to drive the non-sorbed parts of the fluid mixture out of the process microchannels. This may involve using a pressure that is slightly less than the operating pressure being used in the process microchannels during step (A). The pressure differential may be from about 0.1 to about 10 atmospheres below the operating pressure used in the process microchannels during step (A).

Step (B) of the inventive process involves desorbing the sorbed methane or nitrogen from the sorption medium 172. This desorption step may be conducted by increasing or decreasing the temperature within the process microchannels relative to the temperature used during the sorption part of step (A). The pressure used during step (B) may be the same as the pressure used during the sorption part of step (A), or it may be higher or lower. In one embodiment, step (B) is conducted at a higher temperature and a lower pressure than the sorption part of step (A). In one embodiment, the average sorbent temperature used during step (B) may be from about 1° C. to about 200° C., and in one embodiment about 10° C. to about 100° C., above or below the temperature used during the sorption part of step (A). During step (B) the average sorbent temperature within the process microchannels may be in the range from about 0° C. to about 200° C., and in one embodiment about 0° C. to about 200° C., and in one embodiment about 10° C. to about 100° C., and in one embodiment about 40° C. to about 80° C., and in one embodiment about 60° C. during step (B). The pressure within the process microchannels 132 during step (B) may be reduced by about 0.01 to about 10 atmospheres, and in one embodiment about 0.1 to about 1 atmospheres below the pressure used during step (A). Alternatively, the pressure within the process microchannels 132 during step (B) may be raised by about 0.1 to about 10 atmospheres, and in one embodiment about 1 to about 5 atmospheres above the pressure used during step (A). The pressure within the process microchannels during step (B) may be in the range from about 0.0001 to about 100 atmospheres absolute pressure, and in one embodiment from about 0.01 to about 50 atmospheres, and in one embodiment from about 0.1 to about 30 atmospheres, and in one embodiment from about 1 to about 20 atmospheres, and in one embodiment from about 1 to about 10 atmospheres, and in one embodiment from about 1 to about 5 atmospheres absolute pressure. The percentage of sorbed material that is desorbed during this step (B) may range from about 5 to about 100%, and in one embodiment about 10 to about 99% by volume. The time for performing this desorbing step may range from about 0.1 to about 10 seconds, and in one embodiment about 1 second to about 5 seconds.

During step (B) a flush fluid may be used to remove the desorbed methane or nitrogen from the process microchannels 132. The flow of the flush fluid may be simultaneous with the above-described desorption, or it may occur subsequent to such desorption. The start of the flow of flush fluid may be delayed until after the start of the desorption step and then continued after the end of the desorption step. The flush fluid flows into the microchannel separator 100, as indicted by directional arrow 112, to and through process header 104 to the microchannels 132, and then through the microchannels 132 to the process footer 106, and then out of the microchannel separator 100 as indicated by directional arrow 114. The flush fluid may be the same as the methane or nitrogen being separated or it may be a fluid that is non-reactive with the methane or nitrogen. Examples of such non-reactive fluids include water or a condensable hydrocarbon fluid. If the flush fluid is the same as the desorbed methane or nitrogen (for example, if both the flush fluid and the desorbed fluid are methane) then no further separation is required to provide the methane or nitrogen as the desired product from the inventive process. If the flush fluid is not methane or nitrogen, then the flush fluid may be separated from the methane or nitrogen using known techniques (e.g., condensation, evaporation, etc.). Part of the flush fluid may be recirculated to the microchannel separator 100. This process may be continued until a desired removal of methane or nitrogen from the microchannel separator 100 is achieved. The average sorbent temperature within the process microchannels 132 may be in the range from about 0° C. to about 250° C., and in one embodiment about 0° C. to about 200° C., and in one embodiment about 10° C. to about 100° C., and in one embodiment about 40° C. to about 80° C., and in one embodiment about 60° C. during this flushing step. In one embodiment, the average sorbent temperature during the flushing step may be from about 1° C. to about 100° C. higher than the temperature used to desorb the methane or nitrogen during step (B), and in one embodiment from about 10° C. to about 60° C. above the desorption temperature. The pressure within the process microchannels during the flushing step may be in the range from about 0.0001 to about 100 atmospheres absolute pressure, and in one embodiment from about 0.01 to about 50 atmospheres, and in one embodiment from about 0.1 to about 30 atmospheres, and in one embodiment from about 1 to about 20 atmospheres, and in one embodiment about 1 to about 10 atmospheres absolute pressure. The residence time for the flush fluid in the process microchannels during step (B) may be in the range from about 0.1 to about 10 seconds, and in one embodiment about 1 to about 5 second. The pressure drop for the flush fluid flowing through the process microchannels during step (B) may range from about 0.01 to about 10 atmospheres, and in one embodiment about 0.1 to about 1 atmospheres. The Reynolds Number for the flow of the flush fluid through the process microchannels during step (B) may be in the range from about 10 to about 4000, and in one embodiment about 100 to about 2000.

In one embodiment, the requirement for using a flush fluid to remove the desorbed methane or nitrogen may be avoided. In this embodiment, the inlet valves may be closed, and the system heated. The resulting pressurization of the system pushes the desorbed methane or nitrogen out of the process microchannels. In one embodiment, a closed system may be employed where both the inlet and outlet valves are closed during heating, followed by opening the outlet valve to reduce the system pressure and remove the desorbed methane or nitrogen. The outlet valve may also stay open (inlet feed valve closed) during the heating step to begin to remove methane or nitrogen during all or part of the heating step. The heating time and temperature may be tuned to optimize performance. Higher purities and lower capital costs may be achieved with this embodiment. For example, a stream of inlet feed may not be required to flow during desorption to aid in material removal; this would avoid diluting the product. A stream of the product may not be required to be diverted to the desorbing stage and thus diluting the inlet portion of the product stream, nor would it be required to be recompressed to the inlet of the desorber.

In one embodiment, desorbed methane or nitrogen in the process microchannels may be removed using a pressure differential and/or temperature gradient applied across the process microchannels to drive the desorbed methane or nitrogen from the process microchannels. This may involve using a pressure that is slightly less than the operating pressure being used in the process microchannels during step (B). The pressure differential may be from about 0.1 to about 10 atmospheres below the operating pressure used in the process microchannels during step (B).

At the end of step (B) the sorption medium 172 may be regenerated. This may be done by flowing a regenerating fluid through the process microchannels 132 in contact with the sorption medium 172. Examples of suitable regenerating fluids include water, nitrogen, methane and carbon dioxide. The regenerating fluid may flow from the header 104 through the process microchannels 132 and then to the footer 106, or in the opposite direction from the footer 106 through the process microchannels 132 to the header 104. During this regenerating step the average sorbent temperature within the process microchannels may be in the range from about 0° C. to about 250° C., and in one embodiment about 0° C. to about 200° C., and in one embodiment about 10° C. to about 100° C., and in one embodiment about 20° C. to about 80° C., and in one embodiment about 60° C. The pressure within the process microchannels 132 during this regeneration step may be in the range from about 0.0001 to about 100 atmospheres, and in one embodiment about 0.01 to about 50 atmospheres, and in one embodiment about 0.1 to about 30 atmospheres, and in one embodiment about 1 to about 20 atmospheres, and in one embodiment about 1 to about 10 atmospheres absolute pressure. The residence time of the regenerating fluid in the process microchannels 132 may be in the range from about 0.1 to about 10 seconds, and in one embodiment about 1 to about 5 second.

In one embodiment, during the operation of steps (A) and (B) of the inventive process, the process microchannels 132 may be cooled and/or heated using a heat exchange fluid flowing through the heat exchange microchannels 152. The heat exchange channels 152 may switch from cooling during step (A) of the inventive process to heating during step (B). Alternatively, separate dedicated cooling and heating heat exchange microchannels 152 may be used. The heat exchange fluid flows from heat exchange header 108 through the heat exchange microchannels 152 to heat exchange footer 110. The heat exchange fluid transfers heat between the heat exchange microchannels 152 and the process microchannels 132. The heat exchange fluid may be recirculated using known techniques. The heat exchange fluid may be any fluid. These include air, steam, liquid water, gaseous nitrogen, liquid nitrogen, oils such as mineral oil, and heat exchange fluids such as Dowtherm A and Therminol which are available from Dow-Union Carbide.

In one embodiment, the heat exchange microchannels 152 may comprise process microchannels wherein an endothermic or exothermic process is conducted. Examples of endothermic processes that may be conducted in the heat exchange channels include steam reforming and dehydrogenation reactions. In one embodiment, the incorporation of a simultaneous endothermic reaction to provide an improved heat sink may enable a typical heat flux of roughly an order of magnitude or more above the convective cooling heat flux. Examples of exothermic processes that may be conducted in the heat exchange channels include water-gas shift reactions, methanol synthesis reactions and ammonia synthesis reactions.

In one embodiment, the heat exchange fluid undergoes a phase change as it flows through the heat exchange microchannels 152. This phase change provides additional heat addition or removal from the process microchannels or liquid channels beyond that provided by convective heating or cooling. For a liquid heat exchange fluid being vaporized, the additional heat being transferred would result from the latent heat of vaporization required by the heat exchange fluid. An example of such a phase change would be a refrigerant or water that undergoes boiling. In one embodiment, the heat exchange fluid boils or undergoes partial boiling in the heat exchange channels. In one embodiment, the amount of heat exchange fluid boiling in the heat exchange channels may be in the range from about 0.1 to about 99% by volume of the total amount of heat exchange fluid in the heat exchange channel, and in one embodiment about 5 to about 30% by volume.

The heat flux for convective heat exchange or convective heating in the microchannel separator core 102 may be in the range from about 0.01 to about 125 watts per square centimeter ($W/cm^2$) of surface area of the process microchannels in the microchannel separation core, and in one embodiment from about 0.1 to about 50 $W/cm^2$, and in one embodiment from about 1 to about 25 $W/cm^2$, and in one embodiment from about 1 to about 10 $W/cm^2$. The heat flux for phase change heat exchange may range from about 1 to about 250 $W/cm^2$, and in one embodiment, from about 1 to about 100 $W/cm^2$, and in one embodiment from about 1 to about 50 $W/cm^2$, and in one embodiment from about 1 to about 25 $W/cm^2$, and in one embodiment from about 1 to about 10 $W/cm^2$.

The pressure within each individual heat exchange microchannel 152 may be controlled using passive structures (e.g., obstructions), orifices and/or mechanisms upstream of the heat exchange microchannels 152 or in the microchannels. By controlling the pressure within each heat exchange microchannel, the temperature within each heat exchange microchannel can be controlled. A higher inlet pressure for each heat exchange fluid may be used where the passive structures, orifices and/or mechanisms let down the pressure to the desired heat exchange microchannel pressure. By controlling the temperature within each heat exchange microchannel, the temperature in the adjacent process microchannel can be controlled. Thus, for example, each process microchannel may be operated at a desired temperature by employing a specific pressure in the heat exchange microchannel adjacent to the process microchannel. This provides the advantage of precisely controlled temperatures for each process microchannel. The use of precisely controlled temperatures for each process microchannel provides the advantage of a tailored temperature profile and an overall reduction in the energy requirements for the separation process.

The process microchannels 132 may be heated using a resistance heater. The resistance heater may be in the form of heating tape, thin sheets, wire, rods, discs, or similar structures positioned inside the process microchannels 132 or adhered to or embedded in the walls of the process microchannels. Another heating alternative involves using a metal structure such as a metal foam or fin assembly that functions as a resistance heater and is used as a support for the sorption medium 172, the sorbent material being coated on the exterior surface of the metal structure. Another possibility involves using heat conductive particulates (e.g., metallic particulates) intermixed with the sorption medium to control and optimize the overall thermal swing effectiveness. This optimization can be achieved by adjusting the amount and size of the particulates.

In one embodiment, the process microchannels 132 are heated using a resistance heater, and cooled using a heat exchange fluid flowing through heat exchange microchannels 152. The resistance heater may be positioned in the process microchannels 132 or on one side of the process microchannels 132, and the heat exchange microchannels 152 may be positioned on the other side of the process microchannels 132.

In one embodiment, at least about 5% by volume, and in one embodiment from about 5% to about 100% by volume, and in one embodiment from about 10% to about 99% by volume, and in one embodiment from about 25% to about 99% by volume, and in one embodiment from about 50% by about 99% by volume of the fluid mixture that is sorbed during step (A) may be desorbed during step (B).

Figure 14:
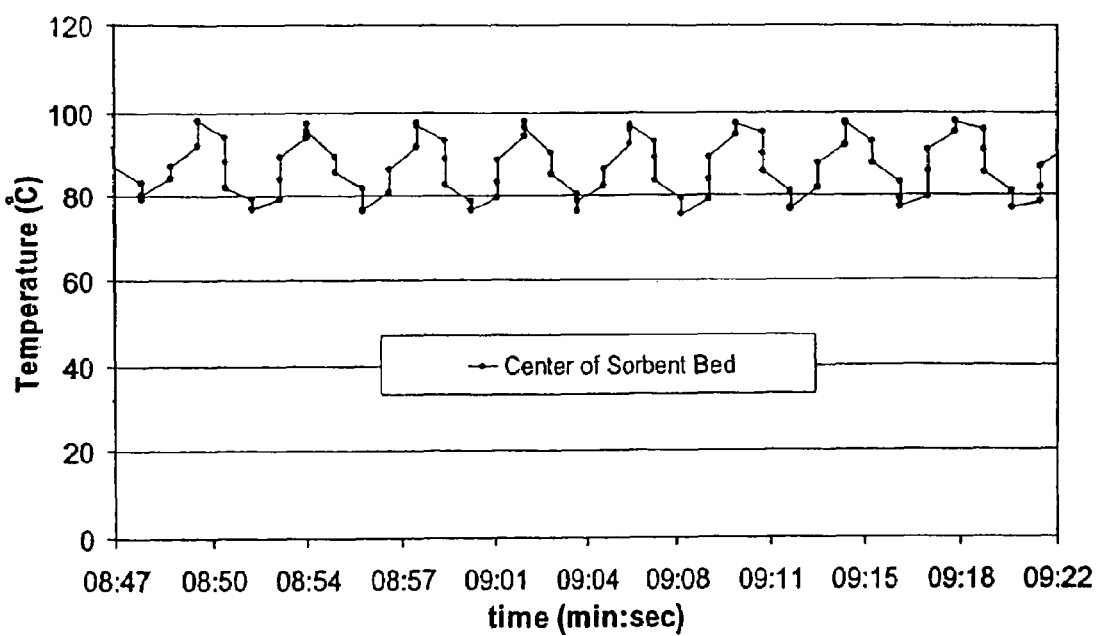
FIG. 14 is a plot of temperature versus time for a microchannel TSA process conducted in accordance with the invention.

In one embodiment, the cycle time required to complete both steps (A) and (B) may be up to about 10 seconds, and in one embodiment from about 0.1 to about 10 seconds, and in one embodiment from about 0.1 to about 8 seconds, and in one embodiment from about 0.2 to about 7 seconds, and in one embodiment from about 0.3 to about 6 seconds, and in one embodiment about 0.5 to about 6 seconds, and in one embodiment about 1 to about 5 seconds, and in one embodiment about 2 to about 5 seconds. In one embodiment, the difference between the average sorbent temperature used in the process microchannels during step (A) and the average sorbent temperature used during step (B) may be in the range from about 1° C. to about 100° C., and in one embodiment about 5° C. to about 75° C., and in one embodiment about 10° C. to about 50° C., and in one embodiment about 10° C. to about 40° C., and in one embodiment about 10° C. to about 30° C., and in one embodiment about 20° C. In one embodiment, the difference in temperature may be about 20° C., and the cycle time may be from about 3 to about 5 seconds. This is illustrated in FIG. 14.

In one embodiment, the average sorbent temperature within the process microchannels during step (A) may be in the range from about 30° C. to about 50° C., and in one embodiment about 35° C. to about 45° C., and in one embodiment about 40° C.; and the average sorbent temperature within the process microchannels during step (B) may be in the range from about 50° C. to about 70° C., and in one embodiment about 55° C. to about 65° C., and in one embodiment about 60° C.

In one embodiment, the flow of the fluid mixture through the process microchannels may be at least about 20 standard cubic meters per hour per cubic meter of volume of the microchannel separator core 102 (SCMH/CM), and in one embodiment from about 20 to about 100 SCMH/CM, and in one embodiment from about 20 to about 50 SCMH/CM, and in one embodiment from about 50 to about 100 SCMH/CM. The recovery of either methane or nitrogen may be at least about 50% by volume of methane or nitrogen in the fluid mixture entering the microchannel separator, and in one embodiment at least about 70% by volume, and in one embodiment at least about 90% by volume.

In one embodiment, the process microchannels 132 may have an internal dimension of height or width of up to about 10 mm, and the heat exchange microchannels 152 may have an internal dimension of height or width of up to about 2 mm. In this embodiment, the relatively large internal height or width of the process microchannels 132 may be used while still allowing relatively fast cycle times if the effective thermal conductivity of the sorption medium 172 is relatively high. For most polymeric or ceramic based sorption mediums, the effective thermal conductivity is on the order of about 1 W/m/K. As the effective thermal conductivity is increased either through the use of co-mixing highly conductive powders or through the use of a highly conductive sorption medium, the height or width of the sorption medium and correspondingly the height or width of the process microchannels 132 may be increased. For effective thermal conductivities of less than about 1 W/m/K, the process microchannels 132 may have an internal height or width of up to about 2 mm. However, as the effective thermal conductivity increases above about 5 W/m/K, the use of larger process microchannels 132 of up to about 10 mm may be used. In these embodiments, heat exchange microchannels 152 may be used to quickly cool the sorption medium 172. A heating microchannel or resistance heating may be used to heat the sorption medium 172.

In one embodiment, a short cycle time may be achieved by the use of process headers 104 and footers 106 that do not contribute substantially to the overall fluid residence time. For example, a one second cycle time may not be achieved if the fluid is retained within the header for 10 seconds. However, if the combined fluid residence time in the header and footer is less than about 0.4 seconds, an overall cycle time of one second may be achieved. In one embodiment, the combined fluid residence time in the process header 104 and process footer 106 may range from about 0.01 to about 1 second, and in one embodiment about 0.1 to about 0.5 second.

The design of headers 104 and footers 106 for fast flush of the fluid mixture, purging fluid and flush fluid requires a balance of short residence times with low header and footer pressure drop to allow for suitable fluid distribution. In one embodiment, the header 104 and footer 106 have geometric designs that enhance the flow of fluid through such headers and footers. Angled headers and footers act to both reduce volume (and thus residence time) and pressure drop to enable good flow distribution. The angle may be in the range of about 5 to about 90 degrees. In addition, open header and footer volumes may be replaced with designs where open volume is only present to directly connect with the process microchannels 132 and is not present above fins, metal plates, and the like. For example, a pipe may be used to distribute fluids from process microchannel to process microchannel (as the pressure drop in a circular or near circular pipe will be lower than rectangular ducts). The flow from the pipe to the process microchannel may be connected via a severe angular entrance region that tapers into a larger rectangular process microchannel. The tapered entrance region advantageously does not overlap fins, metal plates and the like, which may restrict the total volume in the header. Tapered or angular headers have the additional advantage of inhibiting the formation of stagnant areas that are difficult to flush.

In one embodiment, the header may be a multiple entry header which comprises a fluid mixture section, a purging fluid section, and a flush fluid section; the fluid mixture flows from the fluid mixture section into the process microchannels; the purging fluid flows from the purging fluid section into the process microchannels; and the flush fluid flows from the flush fluid section into the process microchannels.

In one embodiment of the invention, a split cycle may be used to tailor the purity of the methane. A split cycle is characterized by opening and closing the valves at the end of the process microchannels at a faster rate than the valves that move the fluid mixture between sorption medium beds. This process increases the methane purity and exhausts the fluid mixture until the purity achieves a desired level. As an example, the feed may alternate between two sorption medium beds at a rate of ten seconds, and split cycle times of one second and nine seconds. During the desorption stage, the purge fluid flows through the sorption medium bed to remove the non-sorbed material and then desorb the desired fluid component. During the first part of the cycle the concentration of the effluent fluid contains components of the entire feed fluid mixture that is retained from the previous feed cycle. The temperature during the first part of the split cycle may either be the sorption temperature or higher than the sorption temperature and approach or equal the desorption temperature. The non-sorbed fluids from the previous feed sorption cycle are removed from the process microchannel sorption medium bed during the first part of the split cycle desorption stage. During this first part of the split cycle the concentration of all components decreases except those sorbed during the previous cycle. The effluent of the first part of the split cycle is sent to an exhaust. When the product purity is sufficiently high to achieve the desired target, the valves are switched at the end of the process microchannels to collect the desorbing fluid effluent as the desired product. The split cycle may be performed at any time during the overall cycle. For a ten second feed cycle time, the split cycle time may be one second, five seconds, or any other value less than ten seconds.

Figure 6:
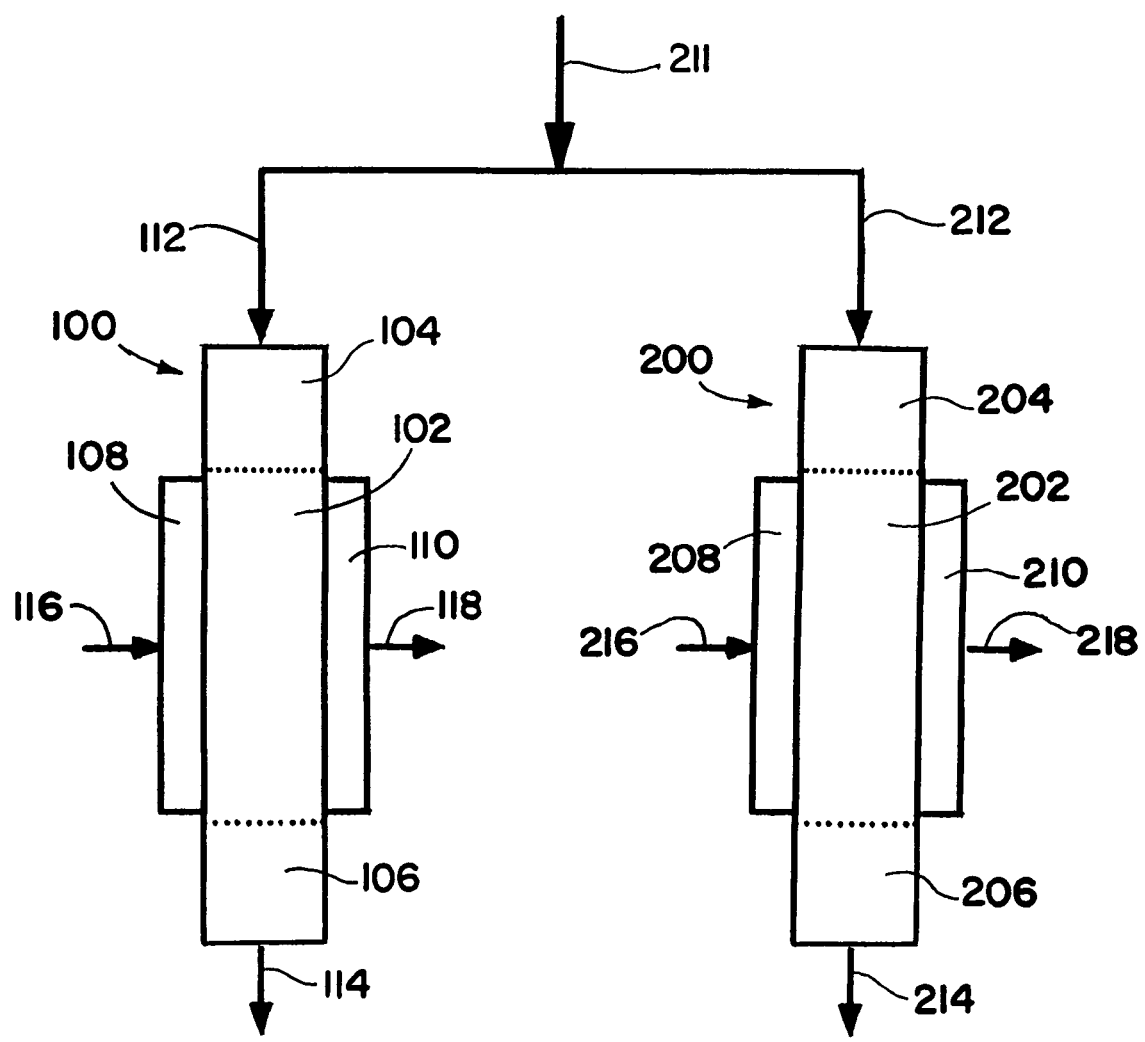
FIG. 6 is a schematic illustration of two microchannel separators which can be operated simultaneously and in parallel pursuant to the inventive process to separate methane or nitrogen from a fluid mixture comprising methane and nitrogen.

The process illustrated in FIG. 6 involves the use of two microchannel separators 100 and 200 operating in parallel. This arrangement allows for a sequential operation wherein step (A) may be conducted in microchannel separator 100 while step (B) is conducted in microchannel separator 200, and vice versa. Microchannel separator 100 is the same as described above with reference to FIG. 2. Microchannel separator 200 is the same as or similar to microchannel separator 100 in construction and operation. Microchannel separator 200 includes microchannel separator core 202, process header 204, process footer 206, heat exchange header 208 and heat exchange footer 210. The microchannel separator core 202 contains a plurality of process microchannels and a plurality of adjacent heat exchange channels. The heat exchange channels may be microchannels. A sorption medium is contained within the process microchannels. The process microchannels and heat exchange channels may be aligned in layers, one above the other, or side by side. A fluid mixture containing methane and nitrogen flows into microchannel separator 200, as indicated by directional arrow 212, through process header 204 and then into the process microchannels in the microchannel separator core 202 where it contacts the sorption medium. The fluid mixture is maintained in the process microchannels in contact with the sorption medium until at least part of either the methane or the nitrogen is sorbed by the sorption medium. The non-sorbed parts of the fluid mixture are then removed from the process microchannels. This may be done by flowing a purging fluid to and through the process header 204, as indicated by directional arrow 212, and then to and through the process microchannels to displace non-sorbed parts of the fluid mixture from the process microchannels. The non-sorbed parts of the fluid mixture and the purging fluid flow through the process microchannels to and through the process footer 206 and out of the microchannel separator 200, as indicated by directional arrow 214. The temperature within the process microchannels is then changed to provide for desorption of the methane or nitrogen from the sorption medium. The methane or nitrogen is desorbed from the sorption medium. The desorbed methane or nitrogen is then removed from the process microchannels. This may be done by flowing a flush fluid into the microchannel separator 200, as indicated by directional arrow 212, to and through process header 204 to the microchannels, and then through the microchannels to the process footer 206, and then out of the microchannel separator 200 as indicated by directional arrow 214. The non-sorbed parts of the fluid mixture may be recycled through the process microchannels any number of times, for example, one, two, three, four times, etc. A heat exchange fluid flows into heat exchange header 208, as indicated by directional arrow 216, and from heat exchange header 208 through the heat exchange channels in microchannel separator core 202 to heat exchange footer 210, and out of heat exchange footer 210, as indicated by directional arrow 218.

The process illustrated in FIG. 6 involves the use of process steps (I)(A), (I)(B), (II)(A) and (II)(B). Step (I)(A) and (I)(B) may be conducted in the same manner as steps (A) and (B) described above with reference to FIG. 2. The only difference is that step (I)(A) initially involves flowing only a portion of the fluid mixture through line 211 to line 112. From that point on the above description of steps (A) and (B) with reference to FIG. 2 are applicable to the description of steps (I)(A) and (I)(B) with reference to FIG. 6.

Step (II)(A) of the process illustrated in FIG. 6 may be conducted by flowing another portion of the fluid mixture through line 211 to line 212, and then through line 212 to microchannel separator 200. In microchannel separator 200 the fluid mixture flows into header 204, the process microchannels in microchannel separator core 204 in contact with a sorption medium, and footer 208. The fluid mixture is maintained in the process microchannels at a desired temperature and pressure to permit at least part of the methane or nitrogen to be sorbed by the sorption medium. This process may be continued until a desired loading of the sorption medium by the methane or nitrogen is achieved. The desired loading level may be in the range of about 0.001 to about 1 gram of methane or nitrogen per gram of sorption medium, and in one embodiment about 0.01 to about 0.1 gram of methane or nitrogen per gram of sorption medium. At the end of this sorption step a purging fluid flows through the header 204, process microchannels and footer 206 to displace the non-sorbed part of the fluid mixture from the microchannel separator 200.

During the sorption part of step (II)(A) in microchannel separator 200 the average sorbent temperature within the process microchannels may be in the range from about −40° C. to about 200° C., and in one embodiment from about −40° C. to about 150° C., and in one embodiment from about 0° C. to about 200° C., and in one embodiment about 20° C. to about 60° C., and in one embodiment from about 30° C. to about 50° C., and in one embodiment about 40° C. The pressure within the process microchannels during step (II)

(A) may be in the range from about 0.0001 to about 100 atmospheres, and in one embodiment from about 0.01 to about 50 atmospheres, and in one embodiment from about 0.1 to about 30 atmospheres, and in one embodiment from about 1 to about 20 atmospheres, and in one embodiment about 1 to about 10 atmospheres absolute pressure. The period of time for the sorption to occur may range from about 0.1 to about 10 seconds, and in one embodiment about 1 to about 5 seconds.

The average sorbent temperature used in the process microchannels to purge the microchannel separator 200 during step (II)(A) may be in the range from about −40° C. to about 200° C., and in one embodiment from about −40° C. to about 150° C., and in one embodiment from 0° C. to about 200° C., and in one embodiment about 20° C. to about 60° C., and in one embodiment from about 40° C. to about 50° C., and in one embodiment about 40° C. In one embodiment, the purging temperature may be in the range from about 1° C. to about 100° C. above the temperature used during the sorption part of step (II)(A), and in one embodiment from about 10° C. to about 60° C. above the step (II)(A) sorption temperature. The residence time for the purging fluid in the process microchannels may be in the range from 0.1 to about 10 seconds, and in one embodiment 1 to about 5 seconds. Examples of purging fluids that may be used include water, methane, nitrogen, condensable fluids, and the like.

Step (II)(B) involves desorbing the sorbed fluid component from the sorption medium in the microchannel separator 200. This desorption step may be conducted by increasing or decreasing the average sorbent temperature of the sorption medium relative to the temperature used during the sorption part of step (II)(A). The pressure used during step (II)(B) may be the same as the pressure used during the sorption part of step (II)(A). In one embodiment, step (II)(B) is conducted at a higher temperature and a lower pressure than the sorption part of step (II)(A). The temperature used in step (II)(B) may be increased by about 1° C. to about 100° C., and in one embodiment about 10° C. to about 60° C., above the temperature that is used during the sorption part of step (II)(A). Alternatively, the temperature used in step (II)(B) may be decreased by about 1° C. to about 100° C., and in one embodiment about 10° C. to about 60° C., below the temperature that is used during the sorption part of step (II)(A). During step (II)(B) the temperature within the process microchannels may be in the range from about 0° C. to about 250° C., and in one embodiment about 0° C. to about 200° C., and in one embodiment about 10° C. to about 100° C., and in one embodiment about 40° C. to about 80° C., and in one embodiment about 60° C. during step (II)(B). The pressure within the process microchannels during step (II)(B) may be reduced by about 0.01 to about 10 atmospheres, and in one embodiment about 0.1 to about 5 atmospheres, below the pressure used during step (II)(A). Alternatively, the pressure within the process microchannels during step (II)(B) may be raised by about 0.1 to about 10 atmospheres, and in one embodiment about 1 to about 5 atmospheres above the pressure used during step (II)(A). The pressure during step (II)(B) may be in the range from about 0.0001 to about 100 atmospheres, and in one embodiment from about 0.01 to about 50 atmospheres, and in one embodiment from about 0.1 to about 30 atmospheres, and in one embodiment from about 1 to about 20 atmospheres, and in one embodiment from about 1 to about 10 atmospheres, and in one embodiment from about 1 to about 5 atmospheres absolute pressure. The percentage of sorbed material that is desorbed during this step (II)(B) may range from about 5% to about 100%, and in one embodiment from about 10 to about 99%. The period of time for performing this desorbing step may range from about 0.1 to about 10 seconds, and in one embodiment about 1 to about 5 seconds.

During step (II)(B) the desorbed methane or nitrogen is removed from the process microchannels. This may be done by flowing a flush fluid through the process microchannels in the microchannel separator 200 to displace the desorbed methane or nitrogen from the process microchannels. The flow of the flush fluid may be simultaneous with the above-described desorption, or it may occur subsequent to such desorption. The start of the flow of the flush fluid may be delayed until after the start of the desorption step and then continued after the end of the desorption step. The flush fluid flows into microchannel separator 200 and within the microchannel separator 200 the flush fluid flows from header 204 through the process microchannels in contact with the sorption medium to footer 206. The flush fluid may be the same as the methane or nitrogen being separated or it may be a fluid that is non-reactive with the methane or nitrogen being separated. The non-reactive fluids may be the same as indicated above. Part of the flush fluid may be recirculated through the microchannel separator 200. This process may be continued until a desired level of removal of the methane or nitrogen from the microchannel separator 200 is achieved.

During the flushing portions of step (II)(B) in the microchannel separator 200 the average sorbent temperature within the process microchannels may be in the range from about 0° C. to about 250° C., and in one embodiment from about 0° C. to about 200° C., and in one embodiment from about 10° C. to about 100° C., and in one embodiment from about 40° C. to about 80° C., and in one embodiment about 60° C. In one embodiment, the average sorbent flush temperature may be from about 10° C. to about 100° C. higher than the temperature used to desorb the methane or nitrogen during step (II)(B), and in one embodiment the flush temperature may be about 20° C. to about 60° C. above the desorption temperature. The pressure within the process microchannels during the flushing step may be in the range from about 0.0001 to about 100 atmospheres, and in one embodiment from about 0.01 to about 50 atmospheres, and in one embodiment from about 0.1 to about 30 atmospheres, and in on embodiment from about 1 to about 20 atmospheres, and in one embodiment about 1 to about 10 atmospheres absolute pressure. The residence time for the flush fluid in the process microchannels during step (II)(B) may range from about 0.1 to about 10 seconds, and in one embodiment about 1 to about 5 seconds. The pressure drop for the flush fluid flowing through the process microchannels during step (II)(B) may range from about 0.01 to about 1 atmospheres, and in one embodiment about 0.05 to about 0.5 atmosphere. The Reynolds Number for the flow of the flush fluid through the process microchannels during step (II)(B) may range from about 10 to about 4000, and in one embodiment about 200 to about 2000.

At the end of step (II)(B) the sorption medium in the microchannel separator 200 may be regenerated. This may be done by flowing a regenerating fluid through the process microchannels in contact with the sorption medium. The regenerating fluid may be water, nitrogen, methane, a condensable fluid, and the like. The regenerating fluid may flow from the header 204 through the process microchannels and then to the footer 206, or in the opposite direction from the footer 206 through the process microchannels to the header 204. The average sorbent temperature within the process microchannels may be in the range from about 0° C. to about 250° C., and in one embodiment about 0° C. to about 200°

C., and in one embodiment about 10° C. to about 100° C., and in one embodiment about 40° C. to about 80° C., and in one embodiment about 60° C. during this regeneration step. In one embodiment, the process microchannels may be cooled at a temperature that is from about 10° C. to about 100° C., and in one embodiment about 20° C. to about 60° C. below the flush temperature used during step (II)(B). The pressure within the process microchannels during this regeneration step may range from about 0.0001 to about 100 atmospheres, and in one embodiment from about 0.01 to about 50 atmospheres, and in one embodiment from about 0.1 to about 30 atmospheres, and in on embodiment from about 1 to about 20 atmospheres, and in one embodiment about 1 to about 10 atmospheres absolute pressure. The residence time for the regenerating fluid in the process microchannels may range from about 0.1 to about 10 seconds, and in one embodiment about 1 second to about 5 seconds.

During the operation of steps (I)(A), (I)(B), (II)(A) and (II)(B) of the process illustrated in FIG. 6, the microchannel separators 100 and 200 may be cooled or heated using heat exchange microchannels, or heated using resistance heating in the same manner as described above. Referring to FIG. 6, during the operation of steps (II)(A) and (II)(B) a heat exchange fluid flows from the exchange header 208 through heat exchange microchannels to heat exchange footer 210. The heat exchange fluid may be recirculated using known techniques. The heat exchange microchannels used in the microchannel separator 200 may have the same dimensions and be made of the same materials as the heat exchange microchannels used in the microchannel separator 100.

In one embodiment, the microchannel separators 100 and 200 may be operated in a sequential manner and in combination with one or more heat exchangers to provide for heating in one of the microchannel separators and at the same time cooling in the other microchannel separator, followed by a reversal from heating to cooling or cooling to heating in the microchannel separators. For example, the inventive process may be operated as a TSA process with cooling during step (I)(A) of the inventive process in microchannel separator 100 in combination with heating during step (II)(B) of the inventive process in microchannel separator 200, followed by a reversal from cooling to heating in microchannel separator 100 to effect step (I)(B) of the inventive process and from heating to cooling in microchannel separator 200 to effect step (II)(A) of the inventive process. In this embodiment, steps (I)(A) and (II)(B) may be conducted simultaneously, and steps (I)(B) and (II)(A) may be conducted simultaneously.

Figure 7:
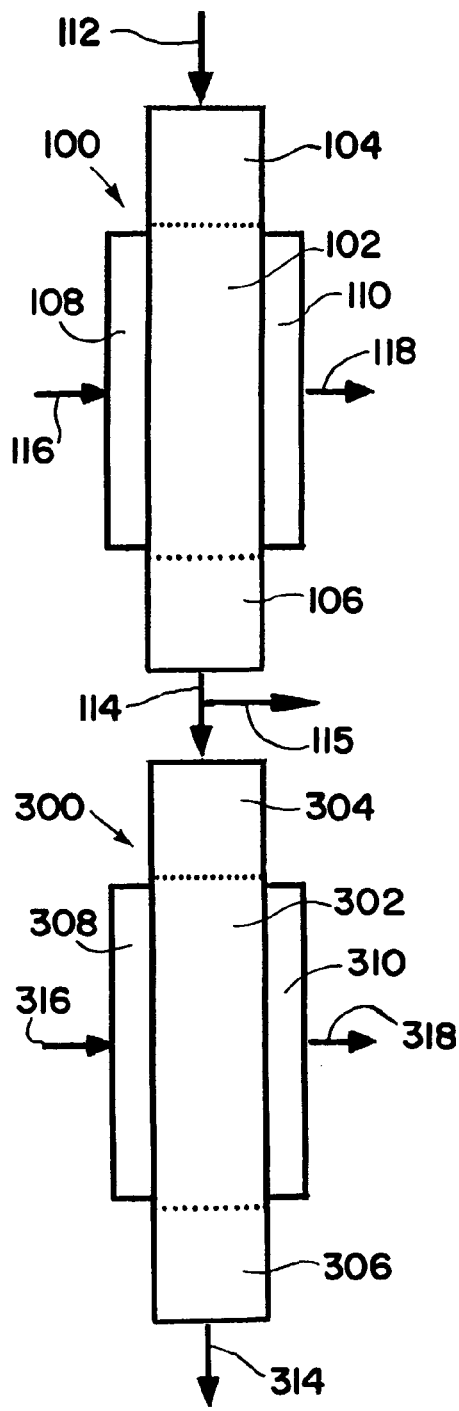
FIG. 7 is a schematic illustration of two microchannel separators which can be operated in series pursuant to the inventive process to separate methane or nitrogen from a fluid mixture comprising methane and nitrogen.

The process illustrated in FIG. 7 involves the use of two microchannel separators 100 and 300 operating in series. This arrangement allows for a sequential operation wherein steps (A) and (B) may be conducted in microchannel separator 100 to provide a first separation of the methane or nitrogen from the fluid mixture, and then repeated in microchannel separator 300 to provide a second separation to provide a more complete separation of the methane or nitrogen from the fluid mixture. Microchannel separator 100 is the same as described above with reference to FIG. 2. Microchannel separator 300 is the same as or similar in construction and operation to microchannel separator 100. Microchannel separator 300 includes microchannel separator core 302, process header 304, process footer 306, heat exchange header 308 and heat exchange footer 310. The microchannel separator core 302 contains a plurality of process microchannels and a plurality of adjacent heat exchange channels. The heat exchange channels may be microchannels. A sorption medium is contained within the process microchannels. The process microchannels and heat exchange channels may be aligned in layers, one above the other, or side by side. A fluid mixture containing methane and nitrogen flows into microchannel separator 300, as indicated by arrow 114, through process header 304 and then into the process microchannels in the microchannel separator core 302 where it contacts the sorption medium. The fluid mixture is maintained in the process microchannels in contact with the sorption medium until at least part of either the methane or the nitrogen is sorbed by the sorption medium. The non-sorbed part of the fluid mixture is then removed from the process microchannels. This may be done by flowing a purging fluid to and through the process header 304, and then to and through the process microchannels to displace non-sorbed parts of the fluid mixture from the process microchannels. The non-sorbed parts of the fluid mixture and the purging fluid flow through the process microchannels to and through the process footer 306 and out of the microchannel separator 300, as indicated by directional arrow 314. The temperature within the process microchannels is then changed to provide for desorption of the methane or nitrogen from the sorption medium. The methane or nitrogen is desorbed from the sorption medium. The desorbed methane or nitrogen is then removed from the process microchannels. This may be done by flowing a flush fluid into the microchannel separator 300 and to and through process header 304 to the microchannels, through the microchannels to the process footer 306, and then out of the microchannel separator 300 as indicated by directional arrow 314. The non-sorbed fluid components may be recycled through the process microchannels any number of times, for example, one, two, three, four times, etc. A heat exchange fluid flows into heat exchange header 308, as indicated by directional arrow 316, and from heat exchange header 308 through the heat exchange channels in microchannel separator core 302 to heat exchange footer 310, and out of heat exchange footer 310, as indicated by directional arrow 318.

The process illustrated in FIG. 7 involves the use of process steps (I)(A), (I)(B), (II)(A) and (II)(B). Step (I)(A) and (I)(B) may be conducted in the same manner as steps (A) and (B) described above with reference to FIG. 2. Thus, the above description of steps (A) and (B) with reference to FIG. 2 are applicable to the description of steps (I)(A) and (I)(B) with reference to FIG. 7.

At the end of step (I)(B), the desorbed methane or nitrogen and flush fluid flow out of the process footer 106, as indicated by arrows 114 and 115. If the flush fluid is not methane or nitrogen, it may be separated from the desorbed methane or nitrogen using conventional techniques. The non-sorbed parts of the fluid mixture removed from microchannel separator 100 during step (I)(A) flow into microchannel separator 300 to commence step (II)(A) of the inventive process. In microchannel separator 300 the fluid mixture flows into header 304, the process microchannels in microchannel separator core 302 in contact with a sorption medium, and footer 308. The fluid mixture is maintained in the process microchannels at a desired temperature and pressure to permit at least part of the methane or nitrogen to be sorbed by the sorption medium. This process may be continued until a desired loading of the sorption medium by the methane or nitrogen is achieved. The desired loading level may be in the range of about 0.001 to about 1 gram of methane or nitrogen per gram of sorption medium, and in one embodiment about 0.01 to about 0.1 gram of methane or nitrogen per gram of sorption medium. At the end of this sorption step the non-sorbed parts of the fluid mixture are removed from the microchannel separator 300. This may be done by flowing a purging fluid through the header 304, process microchannels and footer 306.

During the sorption part of step (II)(A) in microchannel separator 300 the average sorbent temperature within the process microchannels may be in the range from about −40° C. to about 200° C., and in one embodiment from about −40° C. to about 150° C., and in one embodiment from about 0° C. to about 200° C., and in one embodiment about 20° C. to about 60° C., and in one embodiment about 30° C. to about 50° C., and in one embodiment about 40° C. The pressure within the process microchannels during step (II)(A) may be in the range from about 0.0001 to about 100 atmospheres, and in one embodiment from about 0.01 to about 50 atmospheres, and in one embodiment from about 0.1 to about 30 atmospheres, and in on embodiment from about 1 to about 20 atmospheres, and in one embodiment about 1 to about 10 atmospheres absolute pressure. The period of time for the sorption to occur may be in the range from about 0.1 to about 10 seconds, and in one embodiment about 1 to about 5 seconds.

During the purging step temperature that is conducted in microchannel separator 300 during step (II)(A), the average sorbent temperature within the process microchannels may be in the range from about −40° C. to about 200° C., and in one embodiment from about −40° C. to about 150° C., and in one embodiment from about 0° C. to about 200° C., and in one embodiment about 20° C. to about 60° C., and in one embodiment about 30° C. to about 50° C., and in one embodiment about 40° C. In one embodiment, the average sorbent temperature during purging may be about 10° C. to about 110° C. above the temperature used during the sorption part of step (II)(A), and in one embodiment about 20° C. to about 80° C. above the step (II)(A) sorption temperature. The residence time for the purging fluid in the process microchannels may range from 0.1 to about 10 seconds, and in one embodiment 1 to about 5 seconds. Examples of purging fluids that may be used include nitrogen, methane, carbon dioxide, water, condensable fluids, and the like.

Step (II)(B) involves desorbing the sorbed fluid component from the sorption medium in the microchannel separator 300. This desorption step may be conducted by increasing or decreasing the average sorbent temperature within the process microchannels relative to the temperature used during the sorption part of step (II)(A). The pressure used during step (II)(B) may be the same as the pressure used during the sorption part of step (II)(A) or it may be lower or higher. In one embodiment, step (II)(B) may be conducted at a higher temperature and a lower pressure than the sorption part of step (II)(A). The temperature used in step (II)(B) may be increased by about 10° C. to about 200° C., and in one embodiment about 10° C. to about 60° C., above the temperature that is used during the sorption part of step (II)(A). Alternatively, the average sorbent temperature used in step (II)(B) may be decreased by about 10° C. to about 100° C., and in one embodiment about 20° C. to about 60° C., below the average sorbent temperature that is used during the sorption part of step (II)(A). During step (II)(B), the average sorbent temperature within the process microchannels may be in the range from about 0° C. to about 250° C., and in one embodiment about 0° C. to about 200° C., and in one embodiment about 10° C. to about 100° C., and in one embodiment about 40° C. to about 80° C., and in one embodiment about 60° C. to about 80° C. The pressure within the process microchannels during step (II)(B) may be reduced by about 0.01 to about 10 atmospheres, and in one embodiment by about 0.1 to about 1 atmosphere, below the pressure used during step (II)(A). Alternatively, the pressure within the process microchannels during step (II)(B) may be raised by about 0.1 to about 10 atmospheres, and in one embodiment about 1 to about 5 atmospheres above the pressure used during step (II)(A). The pressure during step (II)(B) may be in the range from about 0.0001 to about 100 atmospheres, and in one embodiment from about 0.01 to about 50 atmospheres, and in one embodiment from about 0.1 to about 30 atmospheres, and in on embodiment from about 1 to about 20 atmospheres, and in one embodiment about 1 to about 10 atmospheres absolute pressure. The percentage of sorbed material that is desorbed during this step (II)(B) may range from about 5% to about 100%, and in one embodiment about 10% to about 99%. The period of time for performing this desorbing step may range from about 0.1 to about 10 seconds, and in one embodiment about 1 to about 5 seconds.

During step (II)(B) the desorbed methane or nitrogen is removed from the microchannel separator 300. This may be done by flowing a flush fluid through the process microchannels in the microchannel separator 300 to displace the desorbed methane or nitrogen from the process microchannels. The flow of the flush fluid may be simultaneous with the above-described desorption, or it may occur subsequent to such desorption. The start of the flow of the flush fluid may be delayed until after the start of the desorption step and then continued after the end of the desorption step. The flush fluid flows into microchannel separator 300 and within the microchannel separator 300 the flush fluid flows from header 304 through the process microchannels in contact with the sorption medium to footer 306. The flush fluid may be the same as the methane or nitrogen being separated or it may be a fluid that is non-reactive with the methane or nitrogen being separated. The non-reactive fluids may be the same as indicated above. Part of the flush fluid may be recirculated through the microchannel separator 300. This process may be continued until a desired level of removal of the methane or nitrogen from the microchannel separator 300 is achieved.

During the flushing portion of step (II)(B) the average sorbent temperature within the process microchannels in the microchannel separator 300 may be in the range from about 0° C. to about 250° C., and in one embodiment about 0° C. to about 200° C., and in one embodiment about 10° C. to about 100° C., and in one embodiment about 40° C. to about 80° C., and in one embodiment about 60° C. In one embodiment, the flush average sorbent temperature may be about 10° C. to about 100° C. higher than the temperature used to desorb the methane or nitrogen during step (II)(B), and in one embodiment the flush average sorbent temperature may be about 20° C. to about 60° C. above the average sorbent desorption temperature. The pressure within the process microchannels during the flushing step may range from about 0.0001 to about 100 atmospheres, and in one embodiment from about 0.01 to about 50 atmospheres, and in one embodiment from about 0.1 to about 30 atmospheres, and in on embodiment from about 1 to about 20 atmospheres, and in one embodiment about 1 to about 10 atmospheres absolute pressure. The residence time for the flush fluid in the process microchannels during step (II)(B) may range from about 0.1 to about 10 seconds, and in one embodiment about 1 to about 5 seconds. The pressure drop for the flush fluid flowing through the process microchannels during step (II)(B) may range from about 0.01 to about 10 atmospheres, and in one embodiment about 0.1 to about 1 atmosphere. The Reynolds Number for the flow of the flush fluid through the process microchannels during step (II)(B)

may range from about 10 to about 4000, and in one embodiment about 100 to about 2000.

At the end of step (II)(B) the sorption medium in the microchannel separator 300 may be regenerated. This may be done by flowing a regenerating fluid through the process microchannels in contact with the sorption medium. The regenerating fluid may be nitrogen, methane, water, carbon dioxide, a condensable fluid, and the like. The regenerating fluid may flow from the header 304 through the process microchannels and then to the footer 306, or in the opposite direction from the footer 306 through the process microchannels to the header 304. During this regeneration step the average sorbent temperature within the process microchannels may be in the range from about 0° C. to about 250° C., and in one embodiment about 0° C. to about 200° C., and in one embodiment about 10° C. to about 100° C., and in one embodiment about 40° C. to about 80° C., and in one embodiment about 60° C. In one embodiment, the regenerating temperature may be about 10° C. to about 100° C., and in one embodiment about 20° C. to about 80° C. below the flush temperature used during step (II)(B). The pressure within the process microchannels during this regeneration step may range from about 0.0001 to about 100 atmospheres, and in one embodiment from about 0.01 to about 50 atmospheres, and in one embodiment from about 0.1 to about 30 atmospheres, and in on embodiment from about 1 to about 20 atmospheres, and in one embodiment about 1 to about 10 atmospheres absolute pressure. The residence time for the regenerating fluid in the process microchannels may range from about 0.1 to about 10 seconds, and in one embodiment about 1 second to about 5 seconds.

During the operation of steps (I)(A), (I)(B), (II)(A) and (II)(B) of the process illustrated in FIG. 7, the microchannel separators 100 and 300 may be cooled or heated using heat exchange microchannels, or heated using resistance heating in the same manner as described above. Referring to FIG. 7, during the operation of steps (II)(A) and (II)(B) a heat exchange fluid flows from the exchange header 308 through heat exchange microchannels in the microchannel separator core 302 to heat exchange footer 310. The heat exchange fluid may be recirculated using known techniques. The heat exchange microchannels used in the microchannel separator core 302 may have the same dimensions and be made of the same materials as the heat exchange microchannels used in the microchannel separator core 102.

The sorption medium used in the microchannel separator may have any size and geometric configuration that fits within the process microchannels. The sorption medium may be in the form of particulate solids (e.g., pellets, powder, fibers, and the like) having a median particle diameter of about 1 to about 1000 μm, and in one embodiment about 10 to about 500 μm, and in one embodiment about 25 to about 250 μm. The sorption medium may be supported on a porous support structure such as a foam, felt, wad or a combination thereof. The term "foam" is used herein to refer to a structure with continuous walls defining pores throughout the structure. The term "felt" is used herein to refer to a structure of fibers with interstitial spaces therebetween. The term "wad" is used herein to refer to a structure of tangled strands, like steel wool. The support structure may have a honeycomb construction. The support structure may be the sorbent itself, as in the case of a porous carbon foam. The support structure may also provide mechanical strength for the process microchannel.

The support structure may comprise silica gel, foamed copper, sintered stainless steel fiber, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof.

The sorption medium may be directly washcoated on the interior walls of the process microchannels or onto a support structure. The sorption medium may be in the form of a single piece of porous contiguous material, or many pieces in physical contact. In one embodiment, the sorption medium is comprised of a contiguous material and has a contiguous porosity such that molecules can diffuse through the sorption medium. In this embodiment, the fluids flow through the sorption medium rather than around it. In one embodiment, the cross-sectional area of the sorption medium occupies about 1 to about 99%, and in one embodiment about 10 to about 95% of the cross-sectional area of the process microchannels. The sorption medium may have a surface area, as measured by BET, of greater than about 1 $m^2/g$, and in one embodiment greater than about 10 $m^2/g$. In one embodiment, the sorption medium may have a surface area that exceeds about 100 $m^2/g$. In one embodiment, the surface area may exceed about 1000 $m^2/g$.

Figure 8:
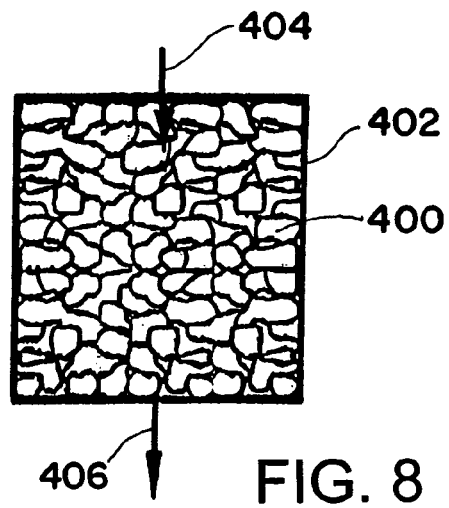
FIG. 8 is a schematic illustration of a cross-sectional view of a process microchannel used with the inventive process, the process microchannel containing a sorption medium having a packed bed configuration.

The sorption medium may be in the form of a packed bed of particulate solids. An example of such a packed bed is illustrated in FIG. 8. In FIG. 8, sorption medium 400, which is in the form of a packed bed of particulate solids, is contained within process microchannel 402. Fluid flows through the packed bed of particulate solids as indicated by arrows 404 and 406.

Figure 9:
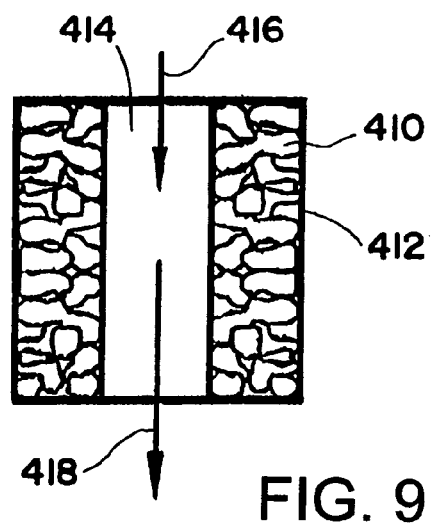
FIG. 9 is a schematic illustration of a cross-sectional view of a process microchannel used with the inventive process, the process microchannel containing a sorption medium having a flow-by configuration.

The sorption medium may be in the form of a flow-by structure such as a felt with an adjacent gap, a foam with an adjacent gap, a fin structure with gaps, a washcoat on any inserted substrate, or a gauze that is parallel to the flow direction with a corresponding gap for flow. An example of a flow-by structure is illustrated in FIG. 9. In FIG. 9, sorption medium 410 is contained within process microchannel 412. An open passage way 414 permits the flow of fluid through the process microchannel 412 in contact with the sorption medium 410 as indicated by arrows 416 and 418.

Figure 10:
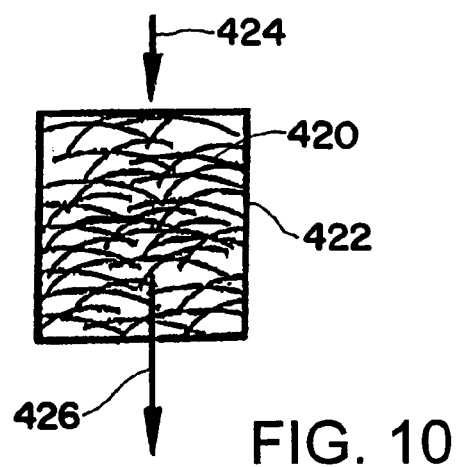
FIG. 10 is a schematic illustration of a cross-sectional view of a process microchannel used with the inventive process, the process microchannel containing a sorption medium having a flow-through configuration.

The sorption medium may be in the form of a flow-through structure such as a foam, wad, pellet, powder, or gauze. An example of a flow-through structure is illustrated in FIG. 10. In FIG. 10, flow-through sorption medium 420 is contained within process microchannel 422 and the fluid flows through the sorption medium 410 as indicated by arrows 424 and 426.

Figure 11:
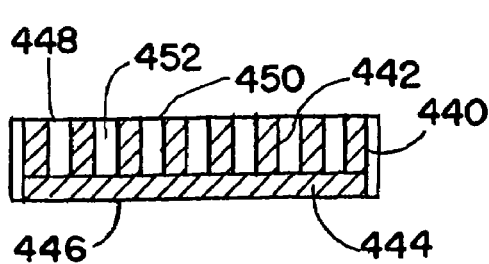
FIG. 11 is a schematic illustration of a process microchannel that may be used in the inventive process, the process microchannel containing a fin assembly comprising a plurality of fins, a sorption medium being supported by the fins.
Figure 12:
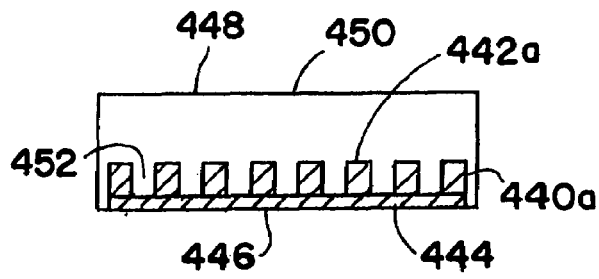
FIG. 12 illustrates an alternate embodiment of the process microchannel and fin assembly illustrated in FIG. 11.
Figure 13:
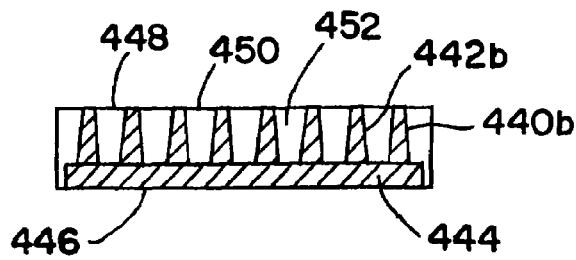
FIG. 13 illustrates another alternate embodiment of the process microchannel and fin assembly illustrated in FIG. 11.

The sorption medium may be supported on an assembly of one or more fins positioned within the process microchannels. Examples are illustrated in FIGS. 11-13. Referring to FIG. 11, fin assembly 440 includes fins 442 which are mounted on fin support 444 which overlies base wall 446 of process microchannel 448. The fins 442 project from the fin support 444 into the interior of the process microchannel 448. The fins 442 extend to and contact the interior surface of upper wall 450 of process microchannel 448. Fin channels 452 between the fins 442 provide passage ways for fluid to flow through the process microchannel 448 parallel to its length. Each of the fins 442 has an exterior surface on each of its sides, this exterior surface provides a support base for the sorption medium. With the inventive process, the fluid mixture flows through the fin channels 452, and contacts the sorption medium supported on the exterior surface of the fins 442. During the inventive process, methane or nitrogen is sorbed onto the supported sorption medium, and then desorbed from the supported sorption medium. The fin assembly 440a illustrated in FIG. 12 is similar to the fin assembly 440 illustrated in FIG. 11 except that the fins 442a do not extend all the way to the interior surface of the upper wall 450 of the microchannel 448. The fin assembly 440b illustrated in FIG. 13 is similar to the fin assembly 440 illustrated in FIG. 11 except that the fins 442b in the fin assembly 440b have cross sectional shapes in the form of trapezoids. Each of the fins may have a height ranging from about 0.02 mm up to the height of the process microchannel 448, and in one embodiment from about 0.02 to about 10 mm, and in one embodiment from about 0.02 to about 5 mm, and in one embodiment from about 0.02 to about 2 mm. The width of each fin may range from about 0.02 to about 5 mm, and in one embodiment from about 0.02 to about 2 mm and in one embodiment about 0.02 to about 1 mm. The length of each fin may be of any length up to the length of the process microchannel 448, and in one embodiment up to about 10 m, and in one embodiment about 0.5 to about 10 m, and in one embodiment about 0.5 to about 6 m, and in one embodiment about 0.5 to about 3 m. The gap between each of the fins may be of any value and may range from about 0.02 to about 5 mm, and in one embodiment from about 0.02 to about 2 mm, and in one embodiment from about 0.02 to about 1 mm. The number of fins in the process microchannel 448 may range from about 1 to about 50 fins per centimeter of width of the process microchannel 448, and in one embodiment from about 1 to about 30 fins per centimeter, and in one embodiment from about 1 to about 10 fins per centimeter, and in one embodiment from about 1 to about 5 fins per centimeter, and in one embodiment from about 1 to about 3 fins per centimeter. Each of the fins may have a cross-section in the form of a rectangle or square as illustrated in FIG. 11 or 12, or a trapezoid as illustrated in FIG. 13. When viewed along its length, each fin may be straight, tapered or have a serpentine configuration. The fin assembly may be made of any material that provides sufficient strength, dimensional stability and heat transfer characteristics to permit operation for which the process microchannel is intended. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof. The fin assembly may be made of an $Al_2O_3$ forming material such as an alloy comprising Fe, Cr, Al and Y, or a $Cr_2O_3$ forming material such as an alloy of Ni, Cr and Fe.

The sorption medium may comprise any sorption medium that sorbs methane or nitrogen with a preferential affinity over the other at one temperature, and then desorbs the methane or nitrogen at a different temperature. In one embodiment, the sorption medium may sorb methane from a fluid mixture containing methane and nitrogen at a temperature in the range of about 0 to about 200° C., and then desorb the methane at a temperature in the range of about 20° to about 400° C. In one embodiment, the sorption medium may sorb methane at a temperature in the range of about 20° C. to about 60° C. from a coal mine gob gas containing methane, nitrogen, carbon dioxide, oxygen and water vapor, and then desorb the methane at a temperature in the range of about 40 to about 100° C. In one embodiment, the sorption medium has a preferential affinity for nitrogen or other coal mine gob gas constituents and allows the methane to pass through. The sorption medium may comprise activated carbon, microporous carbon powder, porous carbon foam, carbon nanotubes, activated aluminia, zeolites, copper metal complexes, metal-organic complexes, or a combination of two or more thereof. In one embodiment, multiple sorbents such as combinations of activated carbon, activated alumina and/or carbon nanotubes may be used.

The sorption medium may comprise activated carbon, also referred to in the art as carbon molecular sieves (CMS). Activated carbon is a useful adsorbent for methane and carbon dioxide with a high selectivity against nitrogen and other gases. Activated carbon with high surface areas in the range from about 10 to about 4000 $m^2/g$, and in one embodiment about 300 to about 3000 $m^2/g$, may be used. The pore volume may range from about 0.1 to about 10 $cm^3/g$, and in one embodiment about 1 to about 5 $cm^3/g$. Useful sources of activated carbon include coal, peat, wood, or coconut shells. The selected particulate size may vary and is a function of the process microchannel size and desired system pressure drop. Suppliers of activated carbon include Amoco, Pica, Calgon, Barnaby Sutcliffe, and Carbotech.

A useful adsorbent is AX-21, which is supplied by Calgon and is in the form of a microporous carbon powder. This material has a surface area of about 3000 $m^2/g$ and a pore volume of about 1.5 $cm^3/g$. Adsorbent results for AX-21 are provided in the following Table 1.

TABLE 1

| Pressure (psig) | Temperature Low (° C.) | Temperature High (° C.) | Differential Capacity $CH_4$ (mg/gm) | Differential Capacity $N_2$ (mg/gm) |
|---|---|---|---|---|
| 2 | 6 | 40 | 14 | 0.9 |
| 2 | 6 | 60 | 17 | 1.1 |
| 2 | 40 | 60 | 3 | 0.2 |
| 100 | 6 | 40 | 21 | 1.9 |
| 100 | 6 | 60 | 31 | 2.2 |
| 100 | 40 | 60 | 10 | 0.3 |

The sorption medium may comprise metal ions that are complexed (e.g., chelated) by ligands. The metal ions may complex with methane or nitrogen. The metal ions that may be used include Fe(II), Co(II), Cu(I), V(II), Mn(II), Mn(III), Cr(II), Ag(I), Rh(I), Rh(II), Rh(III), U(IV), V(IV), Ru(II), Ru(IV), Ti(III), Cr(IV), Bi(III), Ni(II), W(V), W(IV), Mo(II), Mo(III), Mo(IV), Mo(V), Mo(VI), or a combination of two or more thereof. The Roman numerals in the foregoing indicate oxidation states or valence numbers for the ions.

The ligands that may be used to complex the metal ions include dipyridyl; 2,6-[1-(2-imidazol-4-ylethylimino) ethyl pyridine]; cyclen; cyclam; a Schiff base ligand; acetyl acetonate or an oligomer or polymer thereof; a carboxylate; bipyridyl or an oligomer or polymer thereof; a porphyrin or an oligomer or polymer thereof; a corin or an oligomer or polymer thereof; a polyamide; a protein; 8-hydroxy quinoline or an oligomer or polymer thereof; ethyl cysteinate or an oligomer or polymer thereof; an N-alkyl alkanohydroxamic acid; dimethylglyoxime; sym-diethylethylenediamine; or a combination of two or more thereof. The ligands may include fluoride-carbon bonds. The ligands may be fluorinated (e.g., perfluourinated).

The sorption medium may be inorganic. Examples of inorganic sorption mediums that may be used include $Sb_2O_5$, AgO, PtO, $CrO_2$, PbO, HgO, $Cu_2O$, MnO, $Mn_2O_3$, $Bi_2O_4$, NiO, $NiO_2$, $Cu_2O_3$, SnO, $SnO_2$, $WO_2$, $WO_3$, $W_2O_5$, perfluorinated film, Pt/γ-alumina, Fe/γ-alumina, Cu/γ-alumina, Zn/γ-alumina, Co/γ-alumina, zeolite, or a combination of two or more thereof. Included in this group are metal cyanide oligomers and polymers. These include the oligomers and polymers represented by the formulae $[Cu(I)(CN)_x]_n$, $[Fe(II)(CN)_y]_n$, or $[Co(II)(CN)_y]_n$, wherein x is 3; y is 5; and n is a number that is at least 2, and in one embodiment is in the range of about 2 to about 16,500, and in one embodiment about 1000 to about 10,000.

In one embodiment, the process microchannels may be characterized by having a bulk flow path. The term "bulk flow path" refers to an open path (contiguous bulk flow region) within the process microchannels. A contiguous bulk flow region allows rapid fluid flow through the microchannels without large pressure drops. In one embodiment, the flow of fluid in the bulk flow region is laminar. Bulk flow regions within each process microchannel may have a cross-sectional area of about 0.05 to about 10,000 mm$^2$, and in one embodiment about 0.05 to about 5000 mm$^2$, and in one embodiment about 0.1 to about 2500 mm$^2$. The bulk flow regions may comprise from about 5% to about 95%, and in one embodiment about 30% to about 80% of the cross-section of the process microchannels.

The product produced by the inventive process may have a methane concentration of up to about 100% by volume, and in one embodiment about 1 to about 98% by volume, and in one embodiment about 10 to about 90% by volume.

Figure 15:
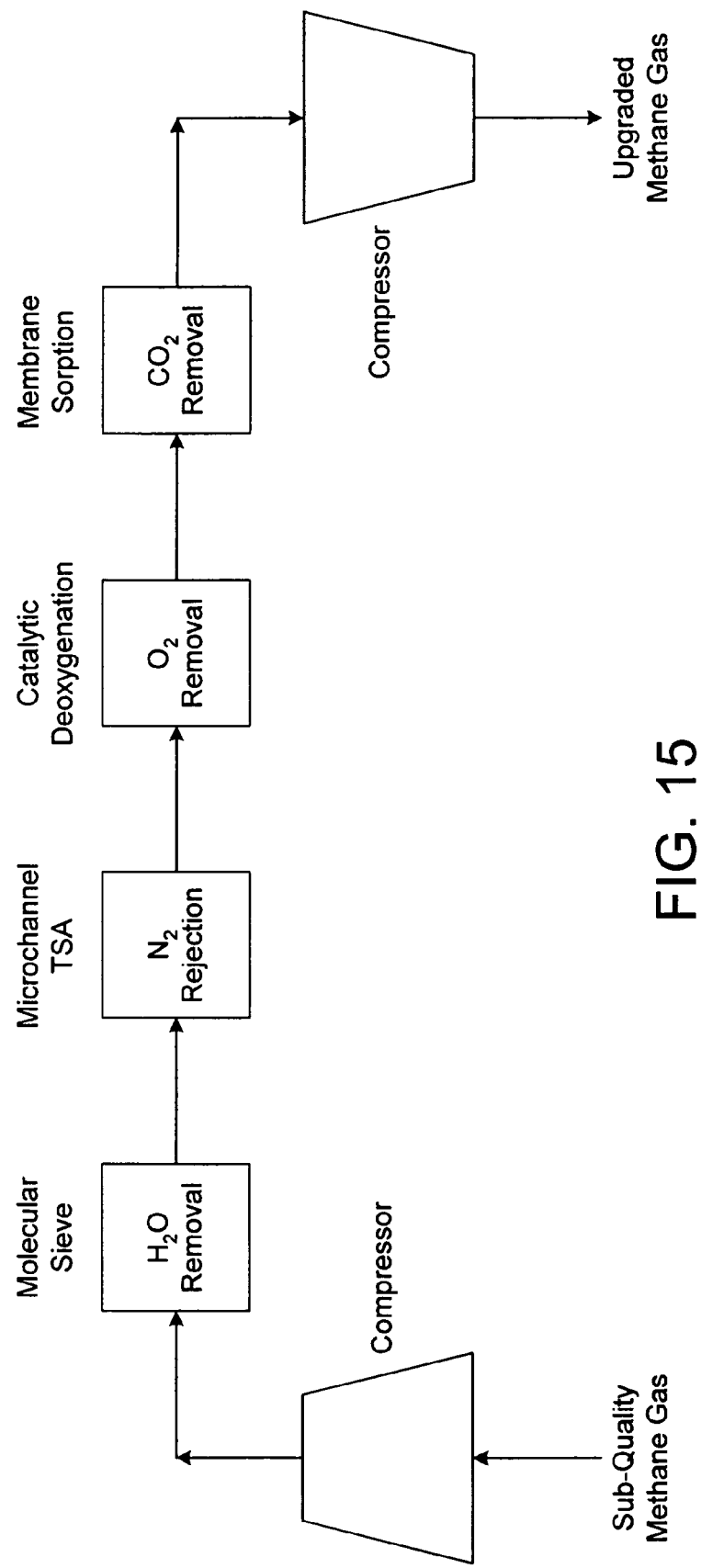
FIG. 15 is a flow diagram illustrating a methane gas upgrading process conducted in accordance with the invention.

In one embodiment, the inventive process can be used in the upgrading of a sub-quality methane gas such as coal mine methane gas. The sub-quality methane gas may comprise methane, water, nitrogen, oxygen, and carbon dioxide. The process is illustrated in FIG. 15. The sub-quality methane gas is compressed in a compressor to a gauge pressure in the range from about 1 to about 50 atmospheres, and in one embodiment about 10 to about 40 atmospheres. The temperature of the sub-quality methane gas may be in the range from about 0° C. to about 200° C., and in one embodiment about 25° C. to about 100° C. The sub-quality methane gas is advanced to a water removal unit wherein water is separated out using conventional techniques, for example, dehydration or filtration using molecular sieves. Examples of the molecular sieves that can be used include: zeolite 5A, 13 X, and the like. The resulting dehydrated sub-quality methane gas is then advanced from the water removal unit to a microchannel TSA nitrogen rejection unit. The microchannel TSA nitrogen rejection unit is a microchannel sorption/desorption unit which can have any of the designs discussed above and be operated using any of the procedures discussed above. In one embodiment, the microchannel TSA nitrogen rejection unit employs microporous carbon powder as the adsorbent, is operated at a pressure in the range from about zero to about 20 atmospheres gauge pressure, and in one embodiment about 6 to about 8 atmospheres gauge pressure, and in one embodiment about 6.8 atmospheres gauge pressure (100 psig), an average sorbent temperature of about 40° C. during the adsorption step (A) and an average sorbent temperature of about 60° C. during the desorption step (B). The adsorbent preferentially adsorbs methane, oxygen and carbon dioxide, and during the adsorption step (A), methane, oxygen and carbon dioxide are adsorbed. The nitrogen may be weakly adsorbed with a capacity at least about 2 times below the methane capacity, and in one embodiment at least about 10 times below the methane capacity. The non or weakly adsorbed nitrogen is removed. The removal of the nonadsorbed or weakly-adsorbed nitrogen may be referred to as a nitrogen rejection step. The average sorbent temperature in the process microchannel is then increased to 60° C. desorb the methane, oxygen and carbon dioxide. The cycle time for completing steps (A) and (B) may be in the range from about 0.1 to about 10 seconds. Alternatively, the microchannel TSA nitrogen rejection unit may be used to reject both nitrogen and water vapor, and thus the initial water vapor removal step would not be required. The desorbed mixture of methane, oxygen and carbon dioxide is advanced to an oxygen removal unit, for example, a catalytic deoxygenation unit, wherein the oxygen is removed. Examples of deoxygenation catalysts that can be used include platinum, palladium, noble metals, and oxides of these metals. In one embodiment, the deoxygenation unit generates heat and this heat may be recovered and used to drive the microchannel TSA nitrogen rejection unit and/or other equipment (e.g., compressors) used in the sub-quality methane gas upgrading process. The remaining mixture of methane and carbon dioxide is advanced to a carbon dioxide removal unit, for example, membrane adsorption unit, wherein carbon dioxide is removed. Examples of the membranes that can be used in the membrane adsorption unit include microporous and polymeric membranes. The final product is an upgraded methane gas. The upgraded methane gas may have a methane concentration in the range from about 90 to about 99.9% by volume, and in one embodiment about 95 to about 99% by volume. The upgraded methane gas may be suitable for use as commercial natural gas. In one embodiment, higher molecular weight hydrocarbons (e.g., ethane, propane, etc.) may be added to the upgraded methane gas to further upgrade marginal quality methane gaseous mixtures. The upgraded methane gas may be advanced through a compressor to a commercial natural gas pipeline or other suitable natural gas storage facility.

An example of a microchannel TSA apparatus that can be used in the nitrogen rejection step for upgrading sub-quality methane gas is illustrated in FIG. 16. The microchannel TSA apparatus 500 is a modular system that contains a plurality of microchannel TSA units 510. Each microchannel TSA unit 510 includes a process microchannel 520 and heat exchange channels 530 and 540. These process microchannels and heat exchange channels can be the same as discussed above. The process microchannel 520 is positioned between the heat exchange channels 530 and 540. The process microchannel 520 contains an adsorbent for preferentially adsorbing methane, and, optionally, oxygen and carbon dioxide, but not nitrogen. One of the heat exchange channels 530 or 540 is used for heating, and the other is used for cooling. During the adsorption phase of the process, i.e. step (A), the average sorbent temperature within the process microchannel 520 may be in the range from about 30° C. to about 50° C., and in one embodiment about 40° C. During the desorption phase of the process, i.e. step (B), the average sorbent temperature within the process microchannel 520 may be in the range of about 40° C. to about 80° C., and in one embodiment about 60° C. The cycle time for completing steps (A) and (B) may be from about 0.1 to about 10 seconds.

The process microchannels 520, and heat exchange channels 530 and 540 may have rectangular cross sections and be aligned in side-by-side vertically oriented interleaved planes or horizontally oriented interleaved stacked planes. These planes can be tilted at an inclined angle from the horizontal. These configurations may be referred to as parallel plate configurations. An array of these rectangular channels can be easily arranged in a modularized compact unit for scale-up.

Figure 17:
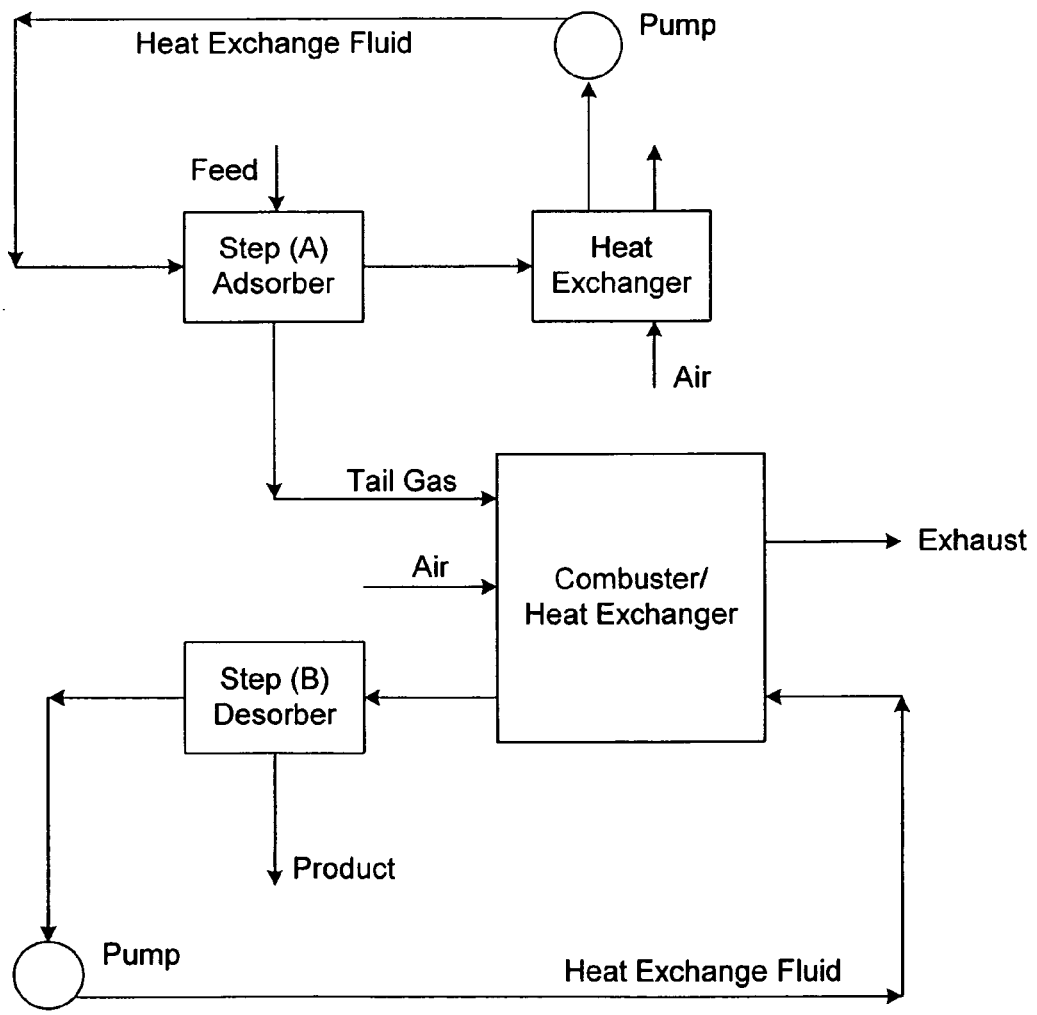
FIG. 17 is a flow diagram illustrating the operation of a microchannel TSA nitrogen rejection unit pursuant to the inventive process.

In one embodiment, less than all of the methane is adsorbed during the adsorption step (A) of the nitrogen rejection process. For example, from about 1 to about 50 percent by volume, and in one embodiment about 1 to about 20 percent by volume of the methane entering the microchannel TSA nitrogen rejection unit may be not be adsorbed during step (A). This results in methane being mixed with the nitrogen that is rejected during step (A). The non-adsorbed gas removed from the microchannel TSA nitrogen rejection unit during step (A) that contains methane can be referred to as a tail gas. The tail gases can be used as an energy source. This is illustrated in FIG. 17. FIG. 17 is a flow sheet illustrating a process for operating the microchannel TSA nitrogen rejection unit. During step (A) of the process, a first heat exchange fluid is circulated through the heat exchange channels 530 for the purpose of providing an average sorbent temperature in the process microchannels in the range from about 30° C. to about 50° C., and in one embodiment about 40° C. The tail gas that is expelled during step (A) is advanced to a combuster/heat exchanger where it is combusted and used to heat a second the heat exchange fluid which is advanced through the heat exchange channels 540 during step (B) of the microchannel TSA process. In one embodiment the tail gas or a portion of the tail gas is combusted within a microchannel. The microchannel combustor may allow more efficient energy recovery and lower NOx production resulting from the shorter time at combustion temperature. During step (B) the average sorbent temperature within the process microchannel may be in the range from about 50° C. to about 70° C., and in one embodiment about 60° C. The use of the tail gas to heat the heat exchange fluid during step (B) provides the microchannel TSA nitrogen rejection unit with an advantage of reduced energy consumption and thereby reduced operating cost.

In the embodiment illustrated in FIG. 17, a two-fluid heat exchange system is used. The two fluid heat exchange system provides more flexibility in terms of choosing heat exchange fluids and requires less compressor power compared to a single fluid heat exchange system. Each heat exchange fluid circulates in a separate heat exchange fluid loop and is heated by a separate heat exchanger. The heat exchange fluids can be in the form of gases or liquids or they can be in the form of two-phase mixtures. One of the heat exchange fluid loops supplies a heat exchange fluid to the heat exchange channels during adsorption, i.e., step (A), and the other heat exchange fluid loop supplies a heat exchange fluid to the heat exchange channels during desorption, i.e., step (B). The pressure within the heat exchange fluid loops may be reduced through valves and recovered through a compressor. The compressor power may be supplied at least in part as a result of combustion of tail gas. For example, in FIG. 17, tail gas is shown as providing an energy source for heating the heat exchange fluid used for desorption.

In one embodiment, energy from the combustion of the tail gas produced during the operation of the microchannel TSA nitrogen rejection unit may be used to operate compressors and/or other equipment used in the upgrading of sub-quality methane gas. The compressor may be used to operate cooling (refrigeration) and/or heating (heat pump) systems to add and/or remove heat from the microchannel TSA nitrogen rejection unit.

The methane upgrading process may require compression to final product pressures in the range from about 1 to about 50 atmospheres absolute pressure, and in one embodiment about 5 to about 40 atmospheres absolute pressure. The compressors used to effect this compression generate heat and typically such heat is rejected to the atmosphere. However, in one embodiment of the invention the heat generated during compression may be used to provide a heat source for the microchannel TSA nitrogen rejection unit. For example, a methane stream containing about 76% by volume methane, about 3% by volume oxygen, about 15% by volume nitrogen, about 3% by volume carbon dioxide, and about 2% by volume water vapor may require a three-stage compressor to increase the pressure from about 2 to about 600 psig (0.14 to 40.8 atmospheres gauge pressure or 1.14 to 41.8 atmospheres absolute pressure). In the first stage the outlet pressure may be about 52.5 psia (3.6 atmospheres absolute pressure), the outlet temperature may be about 149° C. and a 123 horsepower (hp) compressor is required. An interstage cooler recovers about 73 kW to reduce the process temperature to about 49° C. In a second stage compressor, the outlet pressure may be about 177 psia (12 atmospheres absolute pressure), the outlet temperature may be about 185° C., and a 135 hp compressor is required. The second interstage cooler requires about 111 kW to reduce the temperature to about 49° C. The final stage may increase the pressure to about 620 psia (42.4 atmospheres absolute pressure), the outlet temperature may be about 188° C., and a 135 hp compressor is required. The final aftercooler requires about 113 kW to reduce the stream temperature to about 49° C. The sum of the energy available (297 kW) may be converted to energy to drive the microchannel TSA nitrogen rejection unit. In one embodiment, heat from the compressor may be used as an energy source to provide at least part of the heat for heating the process microchannels during the microchannel TSA nitrogen rejection process. In one embodiment, the recovered energy from the compressors may comprise from about 2% to about 100%, and in one embodiment from about 5 to about 25% of the total energy required to heat the process microchannels during the microchannel TSA nitrogen rejection process.

While the invention has been explained in relation to various detailed embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process for separating methane or nitrogen from a fluid mixture comprising methane and nitrogen, the process comprising:
   (A) flowing the fluid mixture into a microchannel separator, the microchannel separator comprising a plurality of process microchannels containing a sorption medium, the sorption medium having a preferential affinity for sorbing methane over nitrogen, the fluid mixture being maintained in the microchannel separator until at least part of the methane is sorbed by the sorption medium, and removing non-sorbed parts of the fluid mixture from the microchannel separator;
   (B) desorbing the methane from the sorption medium and removing the desorbed methane from the microchannel separator; and
   wherein tail gas is produced during step (A).

2. The process of claim 1 wherein the temperature during step (A) is in the range from about 0° C. to about 200° C.

3. The process of claim 1 wherein the temperature during step (B) is in the range from about 20° C. to about 400° C.

4. The process of claim 1 wherein the microchannel separator further comprises a header, the header being a multiple entry header which comprises a fluid mixture section, a purging fluid section, and a flush fluid section; the fluid mixture flows from the fluid mixture section into the process microchannels; a purging fluid flows from the purging fluid section into the process microchannels; and the flush fluid flows from the flush fluid section into the process microchannels.

5. The process of claim 1 wherein the process further comprises the step of regenerating the sorption medium subsequent to step (B).

6. The process of claim 1 wherein the process microchannels are at a first average sorbent temperature during step (A) and a second average sorbent temperature during step (B), the first temperature being lower than the second temperature.

7. The process of claim 1 wherein the process microchannels are at a first average sorbent temperature at the beginning of step (A) and a second average sorbent temperature at the end of step (A), the first temperature being higher than the second temperature.

8. The process of claim 1 wherein the process microchannels are heated using a resistance heater.

9. The process of claim 1 wherein the sorption medium comprises a metal structure that functions as a resistance heater.

10. The process of claim 1 wherein the process microchannels exchange heat with heat exchange channels.

11. The process of claim 10 wherein the heat exchange channels comprise microchannels.

12. The process of claim 10 wherein fluid flowing through the process microchannels flows in a first direction, and a heat exchange fluid flows through the heat exchange channels in a second direction, the second direction being cross current relative to the first direction.

13. The process of claim 1 wherein the process microchannels are made of a material comprising: steel; aluminum; titanium; nickel; platinum; rhodium; copper; chromium; brass; an alloy of any of the foregoing metals; a polymer; ceramics; glass; a composite comprising a polymer and fiberglass; quartz; silicon; or a combination of two or more thereof.

14. The process of claim 10 wherein the heat exchange channels are made of a material comprising: steel; aluminum; titanium; nickel; platinum; rhodium; copper; chromium; brass; an alloy of any of the foregoing metals; a polymer; ceramics; glass; a composite comprising polymer and fiberglass; quartz; silicon; or a combination of two or more thereof.

15. The process of claim 1 wherein the sorption medium is in the form of a flow-by sorption medium.

16. The process of claim 1 wherein the sorption medium is in the form of a flow-through sorption medium.

17. The process of claim 1 wherein the process microchannels have interior surfaces and the sorption medium is coated on the interior surfaces of the process microchannels.

18. The process of claim 1 wherein the sorption medium is in the form of particulate solids.

19. The process of claim 1 wherein the sorption medium is in the form of a foam, felt, wad, gauze, honeycomb, fin assembly, or a combination of two or more thereof.

20. The process of claim 19 wherein the foam, felt, wad, gauze or fin assembly functions as a resistance heater.

21. The process of claim 1 wherein the sorption medium has a serpentine configuration.

22. The process of claim 1 wherein the sorption medium occupies about 1 to about 99 percent of the cross sectional area of at least one cross section of the process microchannel.

23. The process of claim 1 wherein the sorption medium comprises metal-organic complex, copper metal complex, zeolite, activated carbon, microporous carbon powder, porous carbon foam, carbon nanotubes, or a combination of two or more thereof.

24. The process of claim 1 wherein at least about 5% by volume of the methane sorbed during step (A) is desorbed during step (B), the time to complete steps (A) and (B) being up to about 10 seconds.

25. The process of claim 1 wherein the sorption medium is at a first average sorbent temperature during step (A) and a second average sorbent temperature during step (B), the difference between the first temperature and the second temperature being about 1° C. to about 200° C.

26. The process of claim 1 wherein the fluid mixture prior to step (A) comprises methane, nitrogen and carbon dioxide.

27. The process of claim 1 wherein the fluid mixture prior to step (A) comprises methane, nitrogen, carbon dioxide, oxygen and water vapor.

28. The process of claim 1 wherein the concentration of methane in the fluid mixture prior to step (A) is from about 1% to about 98% by volume.

29. The process of claim 1 wherein the fluid mixture comprises a methane containing composition derived from a coal mine or landfill, the process microchannels being at a first average sorbent temperature during step (A) and a second average sorbent temperature during step (B), the first average sorbent temperature being lower than the second average sorbent temperature.

30. The process of claim 1 wherein at least about 50% by volume of the methane in the fluid mixture entering the microchannel separator is recovered.

31. The process of claim 1 wherein the microchannel separator further comprises a microchannel separator core for housing the process microchannels, the flow of the fluid mixture through the process microchannels being at least about 20 standard cubic meters per hour per cubic meter of volume of the microchannel separator core, the recovery of methane or nitrogen from the fluid mixture being at least about 50% by volume of the methane or nitrogen in the fluid mixture entering the microchannel separator.

32. The process of claim 1 wherein the tail gas is used as a source of energy.

33. The process of claim 32 wherein at least a portion of the tail gas is combusted within a microchannel.

34. The process of claim 1 wherein the process microchannels are heated during steps (A) and/or (B) by a heat exchange fluid flowing through heat exchange channels, the heat exchange fluid being heated at least in part by combustion of the tail gas.

35. The process of claim 1 wherein during step (A) a purging fluid flows through the process microchannels to remove non-sorbed parts of the fluid mixture from the microchannel separator.

36. The process of claim 1 wherein during step (A) the temperature and/or pressure within the process microchannels is increased to remove non-sorbed parts of the fluid mixture from the microchannel separator.

37. The process of claim 1 wherein during step (B) a flush fluid flows through the process microchannel to remove desorbed methane or nitrogen from the microchannel separator.

38. The process of claim 1 wherein during step (B) the temperature and/or pressure within the process microchannels is increased to remove desorbed methane from the microchannel separator.

39. A process for separating methane or nitrogen from a fluid mixture comprising methane and nitrogen, the process comprising:

(A) flowing the fluid mixture into a microchannel separator, the microchannel separator comprising a plurality of process microchannels containing a sorption medium, the sorption medium comprising microporous carbon powder, the fluid mixture being maintained in the microchannel separator until at least part of the methane is sorbed by the sorption medium, the time for sorbing methane being in the range from about 0.1 to about 10 seconds, and removing non-sorbed parts of the fluid mixture from the microchannel separator; and (B) desorbing the methane from the sorption medium and removing the desorbed methane from the microchannel separator, the average sorbent temperature in the process microchannels during step (B) being in the range from about 5000 to about 70° C., the average sorbent temperature in the process microchannels during step (A) being in the range from about 30° C. to about 50° C.

40. The process of claim 39 wherein the temperature in the process microchannels during step (A) is about 40° C.

41. The process of claim 39 wherein the temperature in the process microchannels during step (B) is about 60° C.

42. The process of claim 39 wherein tail gas is produced during step (A).

43. The process of claim 42 wherein the tail gas is used as a source of energy.

44. The process of claim 42 wherein the process microchannels are heated during steps (A) and/or (B) by a heat exchange fluid flowing through heat exchange channels, the heat exchange fluid being heated at least in part by combustion of the tail gas.

45. The process of claim 39 wherein the pressure within the process microchannels is in the range from about 6 to about 8 atmospheres gauge pressure.

46. The process of claim 39 wherein the process microchannels are heated during steps (A) and/or (B) and a compressor is used to increase the pressure of the fluid mixture, the compressor producing heat, the heat from the compressor being used as an energy source to provide at least part of the heat for heating the process microchannels.

47. A process for separating methane or nitrogen from a fluid mixture comprising methane and nitrogen, the process comprising:

(A) flowing the fluid mixture into a microchannel separator, the microchannel separator comprising a plurality of process microchannels containing a sorption medium, the fluid mixture being maintained in the microchannel separator until at least part of the methane or nitrogen is sorbed by the sorption medium, and removing non-sorbed parts of the fluid mixture from the microchannel separator; and (B) desorbing the methane or nitrogen from the sorption medium and removing the desorbed methane or nitrogen from the microchannel separator;

wherein the process microchannels are at a first average sorbent temperature during step (A) and a second average sorbent temperature during step (B), the first temperature being higher than the second temperature.

48. A process for separating methane or nitrogen from a fluid mixture comprising methane and nitrogen, the process comprising:

(A) flowing the fluid mixture into a microchannel separator, the microchannel separator comprising a plurality of process microchannels containing a sorption medium, the fluid mixture being maintained in the microchannel separator until at least part of the methane or nitrogen is sorbed by the sorption medium, and removing non-sorbed parts of the fluid mixture from the microchannel separator; and (B) desorbing the methane or nitrogen from the sorption medium and removing the desorbed methane or nitrogen from the microchannel separator;

wherein the process microchannels exchange heat with heat exchange channels, fluid flowing through the process microchannels flows in a first direction, and a heat exchange fluid flows through the heat exchange channels in a second direction, the second direction being cocurrent relative to the first direction.

49. A process for separating methane or nitrogen from a fluid mixture comprising methane and nitrogen, the process comprising:

(A) flowing the fluid mixture into a microchannel separator, the microchannel separator comprising a plurality of process microchannels containing a sorption medium, the fluid mixture being maintained in the microchannel separator until at least part of the methane or nitrogen is sorbed by the sorption medium, and removing non-sorbed parts of the fluid mixture from the microchannel separator; and (B) desorbing the methane or nitrogen from the sorption medium and removing the desorbed methane or nitrogen from the microchannel separator;

wherein the sorption medium is in the form of a flow-by structure with an adjacent gap, a foam with an adjacent gap, a fin assembly with gaps, a washcoat on an inserted substrate, or a gauze that is parallel to the flow direction with a corresponding gap for flow.

50. A process for separating methane or nitrogen from a fluid mixture comprising methane and nitrogen, the process comprising:

(A) flowing the fluid mixture into a microchannel separator, the microchannel separator comprising a plurality of process microchannels containing a sorption medium, wherein the sorption medium comprises microporous carbon powder, the fluid mixture being maintained in the microchannel separator until at least part of the methane or nitrogen is sorbed by the sorption medium, and removing non-sorbed parts of the fluid mixture from the microchannel separator; and (B) desorbing the methane or nitrogen from the sorption medium and removing the desorbed methane or nitrogen from the microchannel separator.

51. A process for separating methane or nitrogen from a fluid mixture comprising methane and nitrogen, the process comprising:

(A) flowing the fluid mixture into a microchannel separator, the microchannel separator comprising a plurality of process microchannels containing a sorption medium, the fluid mixture being maintained in the microchannel separator until at least part of the methane or nitrogen is sorbed by the sorption medium, and removing non-sorbed parts of the fluid mixture from the microchannel separator; and (B) desorbing the methane or nitrogen from the sorption medium and removing the desorbed methane or nitrogen from the microchannel separator;

wherein the sorption medium is derived from Fe(II), Co(II), Cu(I), V(II), Mn(II), Mn(III), Cr(II), Ag(I), Rh(I), Rh(II), Rh(III), U(IV), V(IV), Ru(II), Ru(IV), Ti(III), Cr(IV), Bi(III), Ni(II), W(V), W(IV), Mo(II), Mo(III), Mo(IV), Mo(V), Mo(VI), or a combination of two or more thereof.

52. A process for separating methane or nitrogen from a fluid mixture comprising methane and nitrogen, the process comprising:
- (A) flowing the fluid mixture into a microchannel separator, the microchannel separator comprising a plurality of process microchannels containing a sorption medium, the fluid mixture being maintained in the microchannel separator until at least part of the methane or nitrogen is sorbed by the sorption medium, and removing non-sorbed parts of the fluid mixture from the microchannel separator; and
- (B) desorbing the methane or nitrogen from the sorption medium and removing the desorbed methane or nitrogen from the microchannel separator;
- wherein the sorption medium is derived from: dipyridyl; 2,6-[1-(2-imidazol-4-ylethylimino) ethyl pyridine]; cyclen; cyclam; a Schiff base ligand; acetyl acetonate or an oligomer or polymer thereof; a carboxylate; bipyridyl or an oligomer or polymer thereof; a porphyrin or an oligomer or polymer thereof; a corin or an oligomer or polymer thereof; a polyamide; a protein; 8-hydroxy quinoline or an oligomer or polymer thereof; ethyl cysteinate or an oligomer or polymer thereof; an N-alkyl alkanohydroxamic acid; dimethyiglyoxime; sym-diethylethylenediamine; or a combination of two or more thereof.

53. A process for separating methane or nitrogen from a fluid mixture comprising methane and nitrogen, the process comprising:
- (A) flowing the fluid mixture into a microchannel separator, the microchannel separator comprising a plurality of process microchannels containing a sorption medium, the fluid mixture being maintained in the microchannel separator until at least part of the methane or nitrogen is sorbed by the sorption medium, and removing non-sorbed parts of the fluid mixture from the microchannel separator; and
- (B) desorbing the methane or nitrogen from the sorption medium and removing the desorbed methane or nitrogen from the microchannel separator;
- wherein the sorption medium comprises silica gel, foamed copper, sintered stainless steel fiber, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof.

54. A process for upgrading sub-quality methane gas wherein the sub-quality methane gas comprises methane and nitrogen, the process comprising:
- (A) flowing the sub-quality methane gas into a microchannel separator, the microchannel separator comprising a plurality of process microchannels containing a sorption medium, the sub-quality methane gas being maintained in the microchannel separator until at least part of the methane is sorbed by the sorption medium, and removing non-sorbed parts of the sub-quality methane gas from the microchannel separator; and
- (B) desorbing the methane from the sorption medium and removing the desorbed methane from the microchannel separator;
- wherein the sub-quality methane gas further comprises water vapor and the water vapor is separated from the sub-quality methane gas prior to step (A).

55. A process for upgrading sub-quality methane gas wherein the sub-quality methane gas comprises methane and nitrogen, the process comprising:
- (A) flowing the sub-quality methane gas into a microchannel separator, the microchannel separator comprising a plurality of process microchannels containing a sorption medium, the sub-quality methane gas being maintained in the microchannel separator until at least part of the methane is sorbed by the sorption medium, and removing non-sorbed parts of the sub-quality methane gas from the microchannel separator; and
- (B) desorbing the methane from the sorption medium and removing the desorbed methane from the microchannel separator;
- wherein the sub-quality methane gas further comprises oxygen and/or carbon dioxide and the oxygen and/or carbon dioxide is separated from the sub-quality methane gas subsequent to step (B).

56. A process for separating methane or nitrogen from a fluid mixture comprising methane and nitrogen, the process comprising:
- (A) flowing the fluid mixture into a microchannel separator, the microchannel separator comprising a plurality of process microchannels containing a sorption medium, the sorption medium having a preferential affinity for sorbing methane over nitrogen, the fluid mixture being maintained in the microchannel separator until at least part of the methane is sorbed by the sorption medium, and removing non-sorbed parts of the fluid mixture from the microchannel separator;
- (B) desorbing the methane from the sorption medium and removing the desorbed methane from the microchannel separator;
- wherein the process microchannels exchange heat with heat exchange channels and wherein fluid flowing through the process microchannels flows in a first direction, and a heat exchange fluid flows through the heat exchange channels in a second direction, the second direction being counter current relative to the first direction.

57. A process for separating methane or nitrogen from a fluid mixture comprising methane and nitrogen, the process comprising:
- (A) flowing the fluid mixture into a microchannel separator, the microchannel separator comprising a plurality of process microchannels containing a sorption medium, the sorption medium having a preferential affinity for sorbing methane over nitrogen, the fluid mixture being maintained in the microchannel separator until at least part of the methane is sorbed by the sorption medium, and removing non-sorbed parts of the fluid mixture from the microchannel separator;
- (B) desorbing the methane from the sorption medium and removing the desorbed methane from the microchannel separator; and
- wherein the sorption medium is in the form of particulate solids which are mixed with heat conductive particulate solids to increase the thermal conductivity of the sorption medium.

* * * * *